US011366197B2

(12) United States Patent
Leabman

(10) Patent No.: US 11,366,197 B2
(45) Date of Patent: Jun. 21, 2022

(54) METHODS FOR OPERATING STEPPED FREQUENCY RADAR SYSTEMS WITH DIGITAL DEMULTIPLEXING

(71) Applicant: MOVANO INC., San Ramon, CA (US)

(72) Inventor: Michael A. Leabman, San Ramon, CA (US)

(73) Assignee: Movano Inc., Pleasanton, CA (US)

( * ) Notice: Subject to any disclaimer, the term of this patent is extended or adjusted under 35 U.S.C. 154(b) by 378 days.

(21) Appl. No.: 16/683,158

(22) Filed: Nov. 13, 2019

(65) Prior Publication Data

US 2021/0255299 A1   Aug. 19, 2021

Related U.S. Application Data

(60) Provisional application No. 62/886,642, filed on Aug. 14, 2019, provisional application No. 62/781,523, filed on Dec. 18, 2018.

(51) Int. Cl.
  *G01S 7/292* (2006.01)
  *G01S 13/76* (2006.01)
  (Continued)

(52) U.S. Cl.
  CPC .......... *G01S 7/2925* (2013.01); *A61B 5/021* (2013.01); *A61B 5/05* (2013.01); *G01S 7/0232* (2021.05);
  (Continued)

(58) Field of Classification Search
  CPC ...... G01S 7/2925; G01S 13/106; G01S 13/26; G01S 13/76; G01S 13/88; G01S 13/89; G01S 13/347
  See application file for complete search history.

(56) References Cited

U.S. PATENT DOCUMENTS

| 4,527,161 A | 7/1985 | Wehner |
| 4,851,848 A | 7/1989 | Wehner |

(Continued)

FOREIGN PATENT DOCUMENTS

| WO | 2010131029 A1 | 11/2010 |
| WO | 2017111623 A1 | 6/2017 |

OTHER PUBLICATIONS

Nahar, Sabikun, "Design and Implementation of a Stepped Frequency Continuous Wave Radar System for Biomedical Applications", Masters Thesis, University of Tennessee, Aug. 2018 (Year: 2018).*

(Continued)

*Primary Examiner* — Thomas M Hammond, III
(74) *Attorney, Agent, or Firm* — Loza & Loza, LLP

(57) ABSTRACT

Operating a stepped frequency radar system involves performing stepped frequency scanning across a frequency range using at least one transmit antenna and a two-dimensional array of receive antennas and using frequency steps of a fixed step size, processing a first portion of digital data that is generated from the stepped frequency scanning to produce a first digital output, wherein the first portion of the digital data is derived from frequency pulses that are separated by a first step size that is a multiple of the fixed step size, and processing a second portion of digital data that is generated from the stepped frequency scanning to produce a second digital output, wherein the second portion of the digital data is derived from frequency pulses that are separated by a second step size that is a multiple of the fixed step size, wherein the first multiple is different from the second multiple.

4 Claims, 25 Drawing Sheets

(51) Int. Cl.
| | |
|---|---|
| G01S 13/32 | (2006.01) |
| G01S 13/26 | (2006.01) |
| A61B 5/021 | (2006.01) |
| A61B 5/05 | (2021.01) |
| G01S 7/282 | (2006.01) |
| G01S 13/88 | (2006.01) |
| G01S 13/10 | (2006.01) |
| G01S 13/89 | (2006.01) |
| G01S 7/02 | (2006.01) |
| G01S 7/41 | (2006.01) |
| G01S 13/04 | (2006.01) |
| G01S 13/02 | (2006.01) |
| G01S 7/35 | (2006.01) |
| G01S 7/34 | (2006.01) |
| G01S 13/22 | (2006.01) |
| G01S 13/42 | (2006.01) |

(52) U.S. Cl.
CPC .......... *G01S 7/0234* (2021.05); *G01S 7/282* (2013.01); *G01S 7/412* (2013.01); *G01S 13/04* (2013.01); *G01S 13/106* (2013.01); *G01S 13/26* (2013.01); *G01S 13/32* (2013.01); *G01S 13/76* (2013.01); *G01S 13/88* (2013.01); *G01S 13/887* (2013.01); *G01S 13/89* (2013.01); *G01S 7/023* (2013.01); *G01S 7/34* (2013.01); *G01S 7/35* (2013.01); *G01S 13/0209* (2013.01); *G01S 13/227* (2013.01); *G01S 13/426* (2013.01)

(56) References Cited

U.S. PATENT DOCUMENTS

| | | | |
|---|---|---|---|
| 5,499,029 | A | 3/1996 | Bashforth et al. |
| 6,128,276 | A | 10/2000 | Agee |
| 6,512,737 | B1 | 1/2003 | Agee |
| 6,664,920 | B1 | 12/2003 | Mott et al. |
| 7,936,301 | B2 | 5/2011 | Niedzwiecki |
| 8,884,805 | B2 | 11/2014 | Tomich et al. |
| 9,229,102 | B1 * | 1/2016 | Wright ............... G01S 13/887 |
| 9,408,564 | B2 | 8/2016 | Porch et al. |
| 9,575,560 | B2 | 2/2017 | Poupyrev et al. |
| 9,915,727 | B1 | 3/2018 | Reznack et al. |
| 10,092,207 | B1 | 10/2018 | Windmiller |
| 10,229,328 | B2 | 3/2019 | Nikolova et al. |
| 10,398,370 | B2 | 9/2019 | Boshra et al. |
| 10,478,099 | B2 | 11/2019 | Lor et al. |
| 2004/0232329 | A1 | 11/2004 | Biggs |
| 2006/0267828 | A1 | 11/2006 | Steinway et al. |
| 2007/0035437 | A1 | 2/2007 | Steinway et al. |
| 2008/0100510 | A1 | 5/2008 | Bonthron et al. |
| 2008/0169961 | A1 | 7/2008 | Steinway et al. |
| 2008/0319285 | A1 | 12/2008 | Hancock |
| 2009/0262005 | A1 * | 10/2009 | McNeill ............... G01S 13/9029 342/22 |
| 2009/0273507 | A1 | 11/2009 | Niedzwiecki |
| 2010/0324398 | A1 | 12/2010 | Tzyy-Ping |
| 2011/0012777 | A1 | 1/2011 | Tomich et al. |
| 2011/0221519 | A1 | 9/2011 | Katoh et al. |
| 2012/0062297 | A1 | 3/2012 | Keaveney et al. |
| 2012/0150000 | A1 | 6/2012 | Al-Shamma'A et al. |
| 2013/0297223 | A1 | 11/2013 | Fischer |
| 2014/0134959 | A1 | 5/2014 | Tasic et al. |
| 2015/0226837 | A1 | 8/2015 | Corcos et al. |
| 2015/0263777 | A1 | 9/2015 | Fraden |
| 2015/0287235 | A1 | 10/2015 | Rose |
| 2015/0301167 | A1 | 10/2015 | Sentelle et al. |
| 2016/0041617 | A1 | 2/2016 | Poupyrev |
| 2016/0051171 | A1 | 2/2016 | Pikov et al. |
| 2016/0072933 | A1 | 3/2016 | Cox, II |
| 2016/0097716 | A1 | 4/2016 | Gulati et al. |
| 2016/0231236 | A1 | 8/2016 | Gulati et al. |
| 2016/0252607 | A1 | 9/2016 | Saboo et al. |
| 2016/0320852 | A1 | 11/2016 | Poupyrev |
| 2017/0023673 | A1 | 1/2017 | Mansour et al. |
| 2017/0156646 | A1 | 6/2017 | Gulati et al. |
| 2017/0164878 | A1 | 6/2017 | Connor |
| 2017/0238835 | A1 | 8/2017 | Melamed |
| 2017/0307726 | A1 | 10/2017 | Mazzaro et al. |
| 2017/0363709 | A1 | 12/2017 | Charvat et al. |
| 2018/0046258 | A1 | 2/2018 | Poupyrev |
| 2018/0103906 | A1 | 4/2018 | Gandhi et al. |
| 2018/0120420 | A1 | 5/2018 | McMahon et al. |
| 2018/0196134 | A1 | 7/2018 | Safavi-Naeini et al. |
| 2018/0217252 | A1 | 8/2018 | Noujeim et al. |
| 2018/0303386 | A1 | 10/2018 | Hall et al. |
| 2018/0303417 | A1 | 10/2018 | Mensinger et al. |
| 2018/0306723 | A1 | 10/2018 | Ashrafi |
| 2018/0307314 | A1 | 10/2018 | Connor |
| 2018/0322351 | A1 | 11/2018 | Shaker |
| 2018/0348341 | A1 | 12/2018 | Phelan et al. |
| 2019/0008422 | A1 | 1/2019 | Leath et al. |
| 2019/0064342 | A1 | 2/2019 | Daisy et al. |
| 2019/0064344 | A1 | 2/2019 | Turner |
| 2019/0095602 | A1 | 3/2019 | Setlak et al. |
| 2019/0101870 | A1 | 4/2019 | Pandya et al. |
| 2019/0117068 | A1 | 4/2019 | Thomson et al. |
| 2019/0219368 | A1 | 7/2019 | Baheti et al. |
| 2019/0257933 | A1 | 8/2019 | Nath et al. |
| 2019/0290161 | A1 | 9/2019 | Chase |
| 2019/0298265 | A1 | 10/2019 | Keating et al. |
| 2020/0133398 | A1 | 4/2020 | Williams et al. |

OTHER PUBLICATIONS

Bruen, Danielle et al. "Glucose Sensing for Diabetes Monitoring: Recent Developments", Sensors 2017, 21 pgs.

Cespedes, Fabiola Araujo, "RF Sensing System for Continous Blood Blucose Monitoring", Nov. 2017, 121 pgs.

Cheggoju, Shiva Prasad, "Development of Non-Invasive Glucos Sensor", A Thesis Presented to The Graduate Faculty of the University of Akron, May 2016, 80 pgs.

Gia, Tuan Nguyen, "IoT-based continuous glucose monitoring system: A feasibility study", 8th International Conference on Ambient Systems, Networks and Technologies (ANT-2017), pp. 327-334.

Girão, P. Silva et al. "Microwave Doppler radar in unobtrusive health monitoring", Journal of Physics: Conference Series, file:/// C:/Users/Mark%20Wilson/Downloads/Microwave_Doppler_radar_in_unobtrusive_health_moni.pdf, retrieved Oct. 22, 2018, 11 pgs.

Gonzales, Wilbert Villena, "The Progress of Glucose Monitoring—A Review of Invasive to Minimally and Non-Invasive Tehniques, Devices and Sensors", Sensors 2019, 45 pgs.

IHS, "Wearables and Glucose Monitoring" The New Frontier in Diabetes Management, file:///C:/Users/Mark%20Wilson/Downloads/wearables-and-glucose-monitoring%20(1).pdf, retrieved Jun. 19, 2020, 6 pgs.

Jain, Vipul et al. "A Single-Chip Dual-Band 22-29-GHz/77-81-GHz BiCMOS Transceiver for Automotive Radars", IEEE 2009, 17 pgs.

Klaric-Felic, Gordana et al. "Single-Chip Millimeter-Wave Radar", Article in Microwave Journal—Jan. 2015, 10 pgs.

Lien, Jaime, "Soli: Ubiquitous Gesture Sensing with Millimeter Wave Radar", ACM Trans, Graph, vol. 35, No. 4, Article 142, Jul. 2016, 19 pgs.

Mazlouman, Shahrzad Jalaliet al. Contact-less Monitoring of the Major Blood Vessels Supplying Head and Brain (Carotid Arteries), NSTI-Nanotech 2009, 4 pgs.

Nasr, Ismail et al. "A Highly Integrated 60 GHz 6-Channel transceiver with Antenna in Package for Smart Sensing and Short-Range Communications" IEEE Journal of Solid-State Circuits, vol. 51, No. 9, Sep. 2016, pp. 2066-2076.

Nahar, Sabikun, "Design and Implementation of a Stepped Frequency Continous Wave Radar System for Biomedical Applications", Masters Theses, University of Tennessee, Knoxville, Aug. 2018, 85 pgs.

Omer, Ala Eldin et al. "Glucose Levels Detection Using mm-Wave Radar", SensorsLetters, vol. 2, No. 3, Sep. 2018, 5 pgs.

(56) References Cited

OTHER PUBLICATIONS

Ram, Suresh et al. "Compact Radar Form Factors Accelerate commercial Adoption", Microwaves & RF, Jul. 2016, 2 pgs.

Saha, Shimul et al. "A Glucose sensing System Based on Transmission Measurements at Millimetre Waves using Micro strip Patch Antennas", Scientific Reports 7:6855, Jul. 31, 2017, 11 pgs.

Shaker, George et al. "Non-Invasive Monitoring of Glucose Level Changes Utilizing a mm-Wave Radar System", International Journal of Mobile Human Computer Interaction, vol. 10, issue 3, Jul.-Sep. 2018, 20 pgs.

Siegel, Peter H. et al. "Millimeter-Wave Non-Invasive Monitoring of Glucose in Anesthetized Rats", International Conference on Infrared, Millimeter, and Terhaertz Waves, Tucson, AZ, Sep. 14-19, 2014, 2 pgs.

Smith, John L., "The Pursuit of Noninvasive Glucose: Hunting the Deceitful Turkey", Sixth Edition, Revised and Expanded, 2018, 225 pgs.

Yi, Xiang et al. "A 24/77 GHz Dual-Band Receiver for Automotive Radar Applications", vol. 7, 2019, pp. 48053-48059.

Yilmaz, Tuba et al. "Radio-Frequency and Microwave Techniques for Non-Invasive Measurement of Blood Glucose Levels", Diagnosis 2019, 34 pgs.

International Search Report and Written Opinion, PCT/US19/67271, dated May 28, 2020.

American Diabetes Association, "Economic Costs of Diabetes in the U.S. in 2017", https://doi.org/10.2337/dci18-0007, Mar. 22, 2018, 12 pgs.

Cano-Garcia, Helena et al. "Millimeter-Wave Sensing of Diabetes-Relevant Glucose Concentration Changes in Pigs", J Infrared Milli Terahz Waves (2018) 39: pp. 761-772.

Droitcour, Amy Diane, "Non-Contact Measurement of Heat and Respiration Rates with a Single-Chip Microwave Doppler Radar", A Dissertation Submitted to the Department of Electrical Engineering and the Committee on Graduate Studies of Stanford University, Jun. 2006, 470 pgs.

Nahar, Sabikun, "Design and Implementation of a Stepped Frequency Continous Wave Radar System for Biomedical Applications", Masters Theses, University of Tennessee, Knoxville, 85 pgs.

Omer, Ala Eldin et al. "Blood Glucose Level Monitoring Using and FMCW Millimeter-Wave Radar Sensor", Remote Sensing, 2020, 25 pgs.

Saha, Shimul et al. "A Glucose sensing System Based on Transmission Measurements at Millimetre Waves using Micro strip Patch Antennas", Scientific Reports 7:6855, 11 pgs.

Torp, Hans "Signal processing in Ultrasound Doppler and Color Flow Imaging", http://folk.ntnu.no/htorp/Undervisning/FlowMeas02/papers/EstBloodVel.pdf, retrieved Jun. 19, 2020, 22 pgs.

* cited by examiner

IMPULSE

CHIRP

STEPPED

METHODS FOR OPERATING STEPPED FREQUENCY RADAR SYSTEMS WITH DIGITAL DEMULTIPLEXING

BACKGROUND

Radar detection involves transmitting electromagnetic energy and receiving reflected portions of the transmitted electromagnetic energy. Techniques for transmitting electromagnetic energy in radar systems include impulse, chirp, and stepped frequency techniques. Stepped frequency radar has traditionally been implemented by repeatedly scanning over the same frequency range using the same step size. For example, a frequency burst of stepped frequency pulses over the same frequency range with the same step size and the same number of steps is continuously repeated to implement stepped frequency radar. Although traditional stepped frequency radar works well, there is a need to expand the capabilities of stepped frequency radar.

SUMMARY

A method for operating a stepped frequency radar system is disclosed. The method involves performing stepped frequency scanning across a frequency range using at least one transmit antenna and a two-dimensional array of receive antennas and using frequency steps of a fixed step size, processing a first portion of digital data that is generated from the stepped frequency scanning to produce a first digital output, wherein the first portion of the digital data is derived from frequency pulses that are separated by a first step size that is a multiple of the fixed step size, and processing a second portion of digital data that is generated from the stepped frequency scanning to produce a second digital output, wherein the second portion of the digital data is derived from frequency pulses that are separated by a second step size that is a multiple of the fixed step size, wherein the first multiple is different from the second multiple.

In an embodiment, the first portion of digital data is processed to generate ranging information as the first digital output and the second portion of digital data is processed to generate imaging information as the second digital output. In a further embodiment, the first multiple is larger than the second multiple such that the first step size is larger than the second step size.

Another embodiment, of a method for operating a stepped frequency radar system is disclosed. The method involves performing stepped frequency scanning across a frequency range using at least one transmit antenna and a two-dimensional array of receive antennas and using frequency pulses at individually addressable frequencies, associating a first set of digital data generated from the stepped frequency scanning with a first logical bucket, associating a second set of digital data generated from the stepped frequency scanning with a second logical bucket, wherein the first set of digital data and the second set of digital data include digital data corresponding to different sets of individually addressable frequencies, processing the first set of digital data associated with the first logical bucket to determine a first parameter, and processing the second set of digital data associated with the second logical bucket to determine a second parameter.

In an embodiment, the first parameter includes ranging information and the second parameter includes imaging information.

Another embodiment of a method for operating a stepped frequency radar system is disclosed. The method involves performing stepped frequency scanning across a frequency range using at least one transmit antenna and a two-dimensional array of receive antennas and using frequency steps of a fixed step size, generating digital data that corresponds to the stepped frequency scanning across the frequency range, processing a first portion of the digital data that is generated from the stepped frequency scanning across the frequency range to generate ranging information as a first digital output, wherein the first portion of the digital data is derived from frequency pulses that are separated by a first step size that is a multiple of the fixed step size, and processing a second portion of the digital data that is generated from the stepped frequency scanning across the frequency range to generate imaging information as a second digital output, wherein the second portion of the digital data is derived from frequency pulses that are separated by a second step size that is a multiple of the fixed step size, wherein the first multiple is larger than the second multiple such that the first step size is larger than the second step size.

Other aspects in accordance with the invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As is known in the field, radar detection involves transmitting electromagnetic energy and receiving reflected portions of the transmitted electromagnetic energy. Techniques for transmitting electromagnetic energy in radar systems include impulse, chirp, and stepped frequency techniques.

Figure 1A:
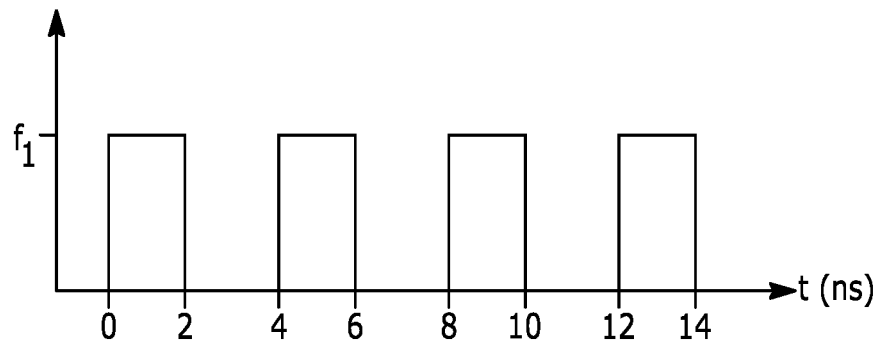
FIGS. 1A-1C depict frequency versus time graphs of impulse, chirp, and stepped frequency techniques for transmitting electromagnetic energy in a radar system.
Figure 1B:
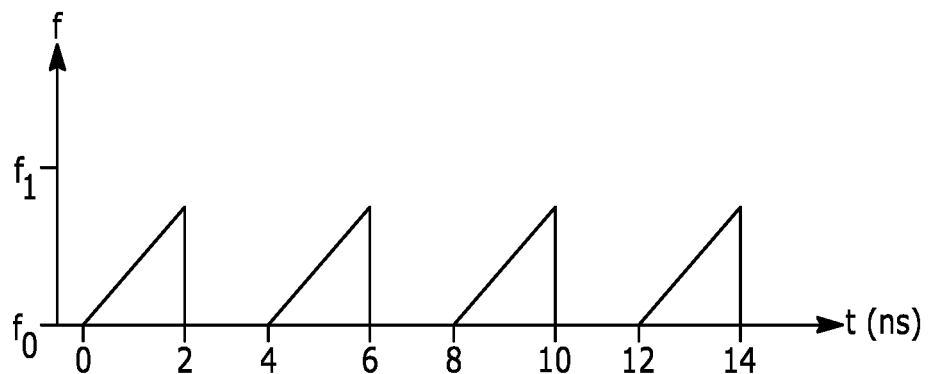
Figure 1C:
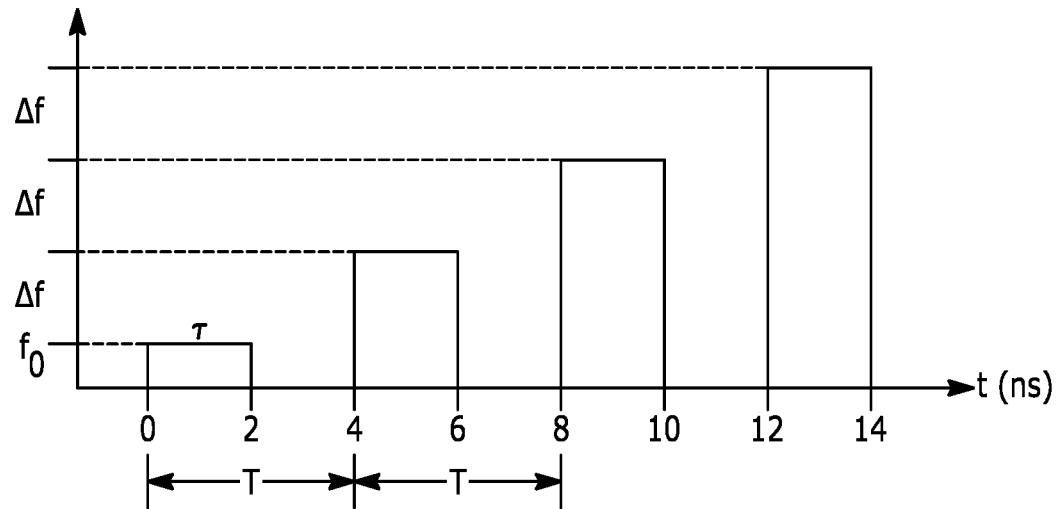

FIGS. 1A-1C depict frequency versus time graphs of impulse, chirp, and stepped frequency techniques for transmitting electromagnetic energy in a radar system. FIG. 1A depicts a radar transmission technique that involves transmitting pulses of electromagnetic energy at the same frequency for each pulse, referred to as "impulse" transmission. In the example of FIG. 1A, each pulse is at frequency, $f_1$, and lasts for a constant interval of approximately 2 ns. The pulses are each separated by approximately 2 ns.

FIG. 1B depicts a radar transmission technique that involves transmitting pulses of electromagnetic energy at an increasing frequency for each interval, referred to herein as "chirp" transmission. In the example of FIG. 1B, each chirp increases in frequency from frequency $f_0$ to $f_1$ over an interval of 2 ns and each chirp is separated by 2 ns. In other embodiments, the chirps may be separated by very short intervals (e.g., a fraction of a nanosecond) or no interval.

FIG. 1C depicts a radar transmission technique that involves transmitting pulses of electromagnetic energy at the same frequency during a particular pulse but at an increased frequency from pulse-to-pulse, referred to herein as a "stepped frequency" transmission or a stepped frequency pattern. In the example of FIG. 1C, each pulse has a constant frequency over the interval of the pulse (e.g., over 2 ns), but the frequency increases by an increment of $\Delta f$ (referred to as a "step size") from pulse-to-pulse. For example, the frequency of the first pulse is $f_0$, the frequency of the second pulse is $f_0+\Delta f$, the frequency of the third pulse is $f_0+2\Delta f$, and the frequency of the fourth pulse is $f_0+3\Delta f$, and so on.

Figure 2:
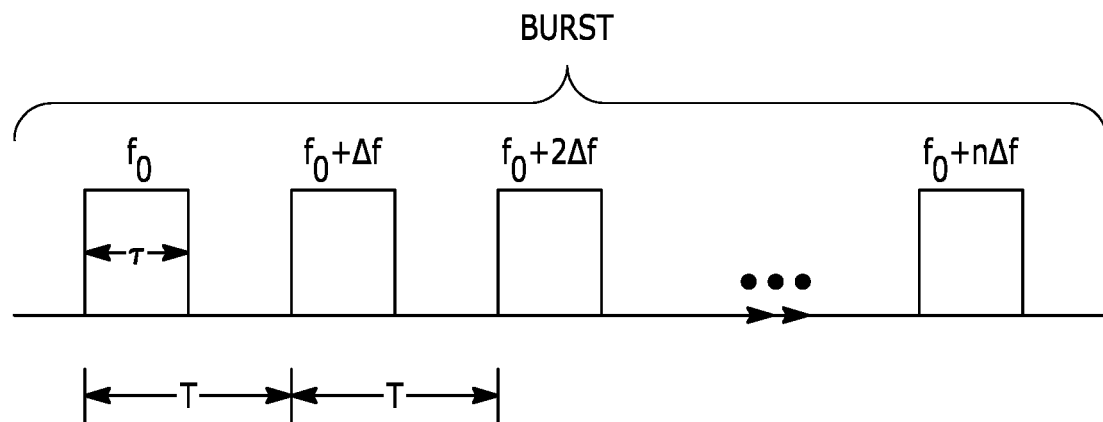
FIG. 2 depicts a burst of electromagnetic energy using stepped frequency transmission.

In an embodiment, the sensor system described herein is operated using stepped frequency transmissions to implement stepped frequency scanning. Operation of the sensor system using stepped frequency transmissions to implement stepped frequency scanning is described in more detail below. FIG. 2 depicts a burst of electromagnetic energy over a frequency range that includes multiple steps using stepped frequency transmission. The frequency of the pulses in the multi-step burst can be expressed as:

$$f_n = f_0 + n\Delta f$$

where $f_0$=starting carrier frequency, $\Delta f$=step size, $\tau$=pulse length (active, per frequency), T=repetition interval, n=1,...N, each burst consists of N pulses (frequencies) and a coherent processing interval (CPI)=N·T=1 full burst. In an embodiment, the repetition interval corresponds to the sweep rate of the stepped frequency scanning and the width of the full burst is referred to as the frequency range or the stepped frequency scanning range.

Using stepped frequency scanning enables relatively high range resolution. High range resolution can be advantageous in ranging and 3D radar imaging, which can have applications such as identifying objects, e.g., a weapon on a person that may, for example, be made of a reflective material and that may have a size in the range of 25 cm×12 cm, e.g., the size of a typical handgun. In an embodiment, in order to effectively isolate a signal that corresponds to reflections of electromagnetic energy from an object such as a hand-held weapon, it is desirable to have a corresponding range resolution, which may be provided by the 2-6 GHz frequency range.

Using stepped frequency scanning, range resolution can be expressed as:

$$\Delta R = c/2B$$

wherein c=speed of light, B=effective bandwidth. The range resolution can then be expressed as:

$$\Delta R = c/2N\cdot\Delta f$$

wherein B=N·$\Delta f$. Thus, range resolution does not depend on instantaneous bandwidth and the range resolution can be increased arbitrarily by increasing N·$\Delta f$.

Figure 3A:
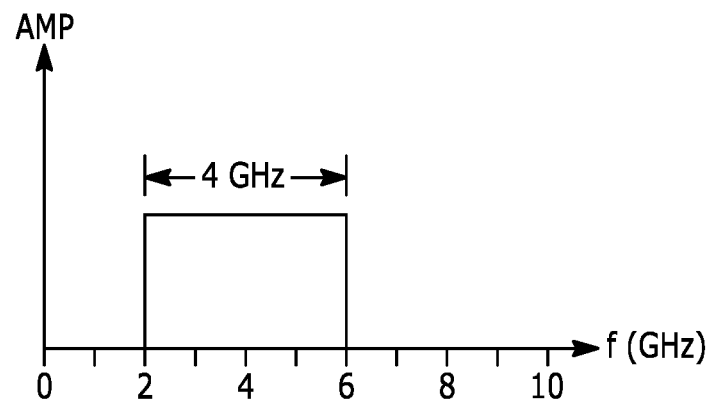
FIG. 3A depicts a graph of the transmission bandwidth, B, of transmitted electromagnetic energy in the frequency range of 2-6 GHz.

In an embodiment, electromagnetic energy is transmitted from at least one antenna (referred to as a "TX antenna") of a stepped frequency radar system in the frequency range of approximately 2-6 GHz, which corresponds to a total bandwidth of approximately 4 GHz, e.g., B=4 GHz. FIG. 3A depicts a graph of the transmission bandwidth, B, of transmitted electromagnetic energy in the frequency range of 2-6 GHz. Within a 4 GHz bandwidth, from 2-6 GHz, discrete frequencies (e.g., frequency pulses each centered at a different frequency) can be transmitted. For example, in an embodiment, the number of discrete frequencies that can be transmitted ranges from, for example, 64-1,024 discrete frequencies, e.g., 64, 128, 256, 512, or 1,024 discrete frequencies. In a case in which 64 discrete frequencies are available and a repetition interval, T, over 4 GHz of bandwidth, the step size, $\Delta f$, is 62.5 MHz (e.g., 4 GHz of bandwidth divided by 64=62.5 MHz) and in a case with 256 discrete frequencies available and a repetition interval, T, over 4 GHz of bandwidth, the step size, $\Delta f$, is 15.625 MHz (e.g., 4 GHz of bandwidth divided by 256=15.625 MHz).

Figure 3B:
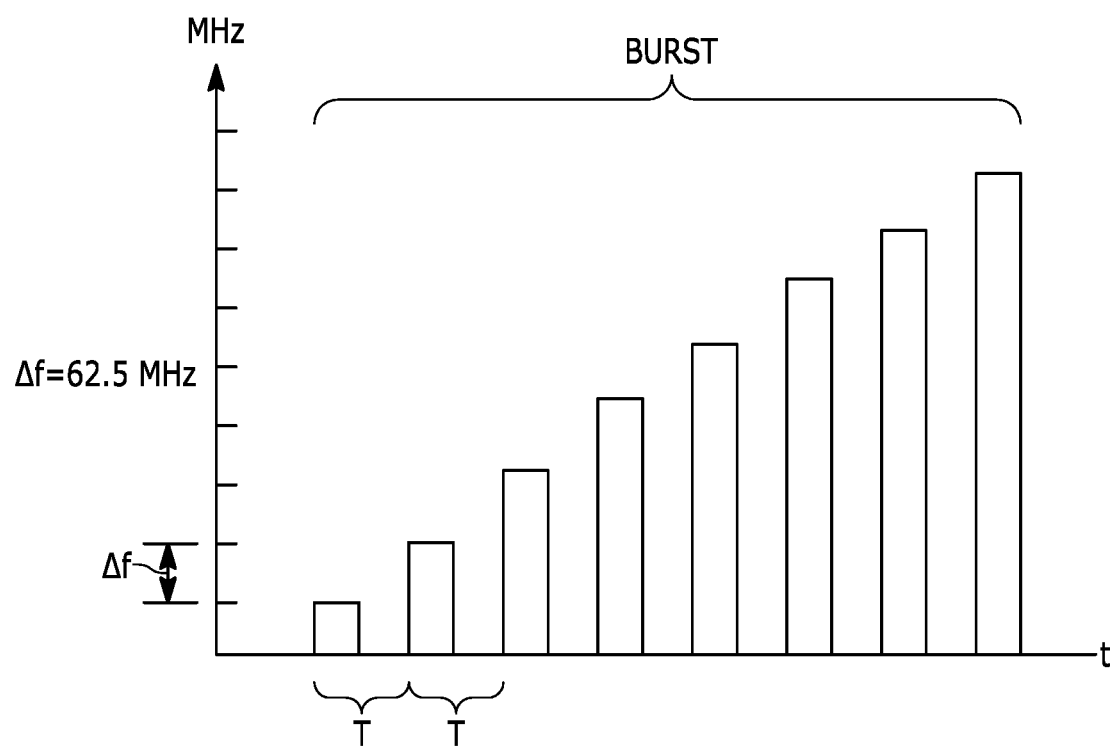
FIG. 3B depicts a graph of stepped frequency pulses that have a repetition interval, T, and a step size, Δf, of 62.5 MHz.

FIG. 3B depicts a graph of stepped frequency pulses that have a repetition interval, T, and a step size, $\Delta f$, of 62.5 MHz (e.g., 4 GHz of bandwidth divided by 64=62.5 MHz). As is described below, an example sensor system may have two TX antennas and four receive (RX) antennas. Assuming a discrete frequency can be received on each RX antenna, degrees of freedom (DOF) of the sensor system in the receive operations can be expressed as: 4 RX antennas×64 discrete frequencies=256 DOF; and 4 RX antennas×256 discrete frequencies=1K DOF. The number of degrees of freedom (also referred to as "transmission frequency diversity") can provide signal diversity, which can be beneficial in 3D radar imaging. For example, the different discrete frequencies may have different responses to different objects, e.g., different types of weapons. Thus, greater transmission frequency diversity can translate to greater signal diversity, and ultimately to more accurate 3D radar imaging.

Figure 4A:
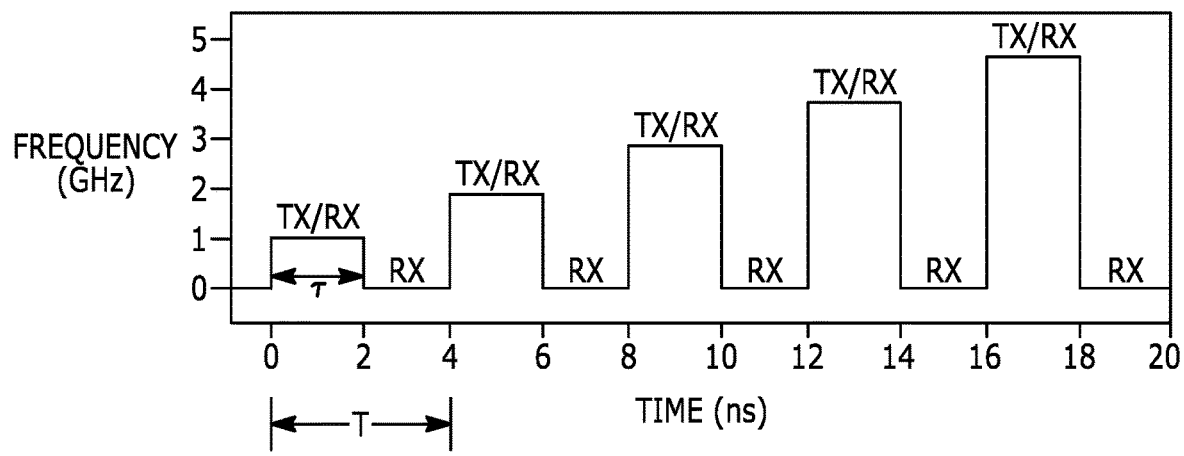
FIG. 4A depicts a frequency versus time graph of transmission pulses, with transmit (TX) interval and receive (RX) intervals identified relative to the pulses.
Figure 4B:
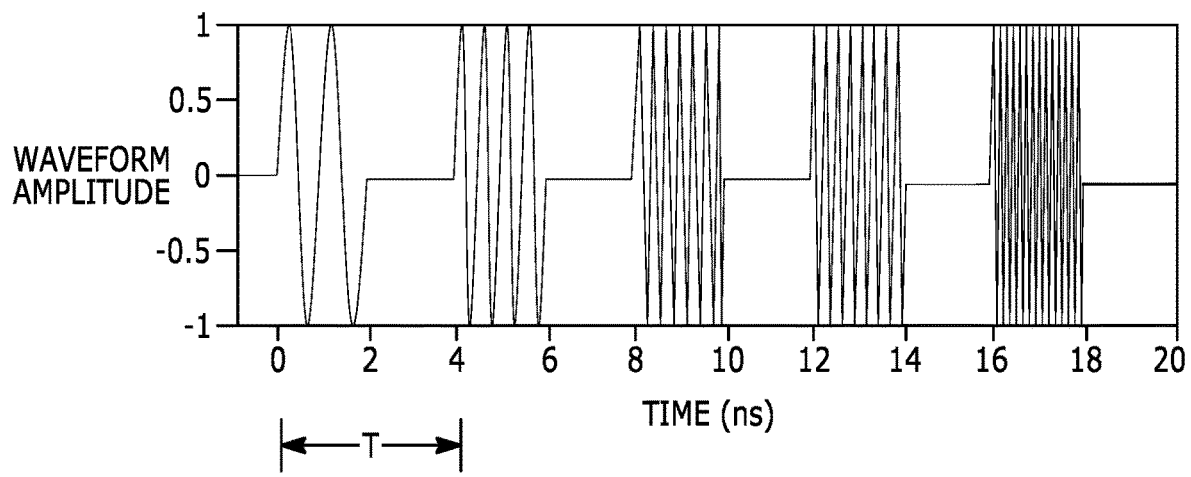
FIG. 4B depicts an amplitude versus time graph of the transmission waveforms that corresponds to FIG. 16A.

One feature of stepped frequency radar is that the sensor system receives reflected electromagnetic energy at basically the same frequency over the repetition interval, T. That is, as opposed to chirp transmission, the frequency of the pulse does not change over the interval of the pulse and therefore the received reflected electromagnetic energy is at the same frequency as the transmitted electromagnetic energy for the respective interval. FIG. 4A depicts stepped frequency scanning as a frequency versus time graph of transmission pulses, with transmit (TX) and receive (RX) intervals identified relative to the pulses. As illustrated in FIG. 4A, RX operations for the first pulse occur during the pulse length, $\tau$, of repetition interval, T, and during the interval between the next pulse. FIG. 4B depicts an amplitude versus time graph of the transmission waveforms that corresponds to FIG. 4A. As illustrated in FIG. 4B, the amplitude of the pulses is constant while the frequency increases by $\Delta f$ at each repetition interval, T.

In an embodiment, the power of the transmitted electromagnetic energy can be set to achieve a desired transmission distance and/or a desired. In an embodiment, the transmission power from the TX antennas is about 20 dBm.

In an embodiment, electromagnetic energy can be transmitted from the TX antennas one TX antenna at a time (referred to herein as "transmit diversity"). For example, a signal is transmitted from a first one of two TX antennas while the second one of the two TX antennas is idle and then a signal is transmitted from the second TX antenna while the first TX antenna is idle. Transmit diversity may reveal that illumination from one of the two TX antennas provides a higher quality signal than illumination from the other of two TX antennas. This may be especially true when trying to identify an object such as a person or a weapon carried by a person. Thus, transmit diversity can provide sets of received signals that are independent of each other and may have different characteristics, e.g., signal power, SNR, etc.

Some theory related to operating a stepped frequency radar system to implement stepped frequency scanning is described with reference to FIG. 5, which illustrates operations related to transmitting, receiving, and processing phases of a sensor system operation. With reference to the upper portion of FIG. 5, a time versus amplitude graph of a transmitted signal burst, similar to the graph of FIG. 4B, is shown. The graph represents the waveforms of five pulses of a burst at frequencies of $f_0$, $f_0+\Delta f$, $f_0+2\Delta f$, $f_0+3\Delta f$, and $f_0+4\Delta f$.

Figure 5:
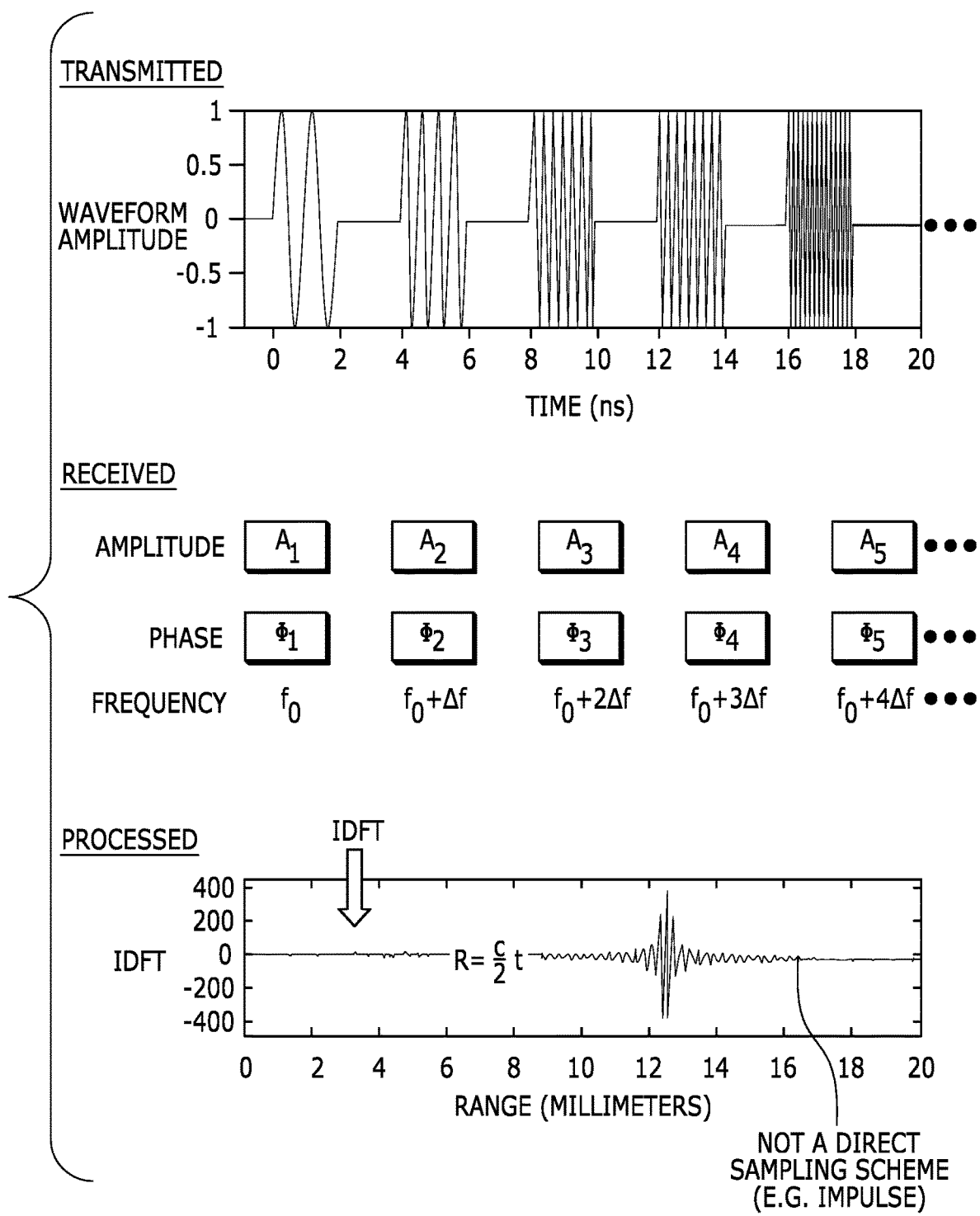
FIG. 5 illustrates operations related to transmitting, receiving, and processing phases of the sensor system operation.

The middle portion of FIG. 5 represents values of received signals that correspond to the amplitude, phase, and frequency of each pulse in the burst of four pulses. In an embodiment, received signals are placed in range bins such that there is one complex sample per range bin per frequency. Inverse Discrete Fourier Transforms (IDFTs) are then performed on a per-range bin basis to determine range information. The bottom portion of FIG. 5 illustrates an IDFT process that produces a signal that corresponds to the range of a particular object. For example, the range may correspond to an object such as a person or a weapon carried by a person. In stepped frequency radar, the process of transmitting the frequency pulses in bursts of N pulses is repeated over the same frequency range to determine the range of object. Additionally, the process can be repeated using a 2D array of receive antennas to obtain 2D information that can be used for 2D and/or 3D imaging. In an embodiment, some portion of the signal processing is performed digitally by a DSP or CPU. Although one example of a signal processing scheme is described with reference to FIG. 5, other signal processing schemes may be implemented to isolate signals that correspond to reflections from objects of interest from signals that correspond to reflections from other undesired objects and from signals that correspond to leakage from the TX antennas.

As described above with reference to FIGS. 1C-5, stepped frequency radar scanning is typically implemented by repeatedly scanning over the same frequency range (e.g., one full burst) with multiple RF pulses that increase in frequency by the same step size. For example, with reference to FIGS. 3B, 4A, and 4B, a frequency burst of stepped frequency pulses over the same frequency range with the same step size and the same number of steps is repeatedly transmitted to implement stepped frequency scanning. However, it has been realized that digital control of discrete frequencies in a stepped frequency radar system enables approaches to stepped frequency RF scanning and applications for stepped frequency radar that heretofore have not been envisioned. For example, digital control of discrete frequencies in a stepped frequency radar system enables the step size, frequency range, and/or discrete frequencies to be changed during a stepped frequency scanning operation in various unique ways. In an embodiment, the step size can be changed to a smaller step size to, for example, provide greater imaging resolution within a particular frequency band of interest. In some instances, the step size can be changed "on-the-fly" in response to feedback from the stepped frequency scanning and in other instances a change in step size can be preprogrammed. In another embodiment, the scanned frequency range can be changed to avoid, or "hop" over, a frequency band that may interfere with the scanning operation. Frequency hopping may be implemented to, for example, avoid frequency bands that are known to cause interference and/or frequency hopping may be adapted to avoid interfering frequency bands that are learned by the system. In another embodiment, simultaneous stepped frequency scanning for ranging and stepped frequency scanning for imaging (e.g., 2D or 3D imaging) can be accomplished by selectively associating digital scanning data with different ranging and imaging data buckets for digital processing. In another embodiment, interference between two stepped frequency radar systems can be mitigated by encoding the discrete frequencies of the stepped frequency scanning (e.g., in a pseudorandom manner) so that frequency pulses at the same frequency are unlikely to be transmitted by two stepped frequency radar systems at the same time. As is described below, digital control of discrete frequencies in a stepped frequency radar system provides spectral agility that can be utilized to implement approaches to stepped frequency scanning and applications for stepped frequency radar that heretofore have not been envisioned.

Figure 6:
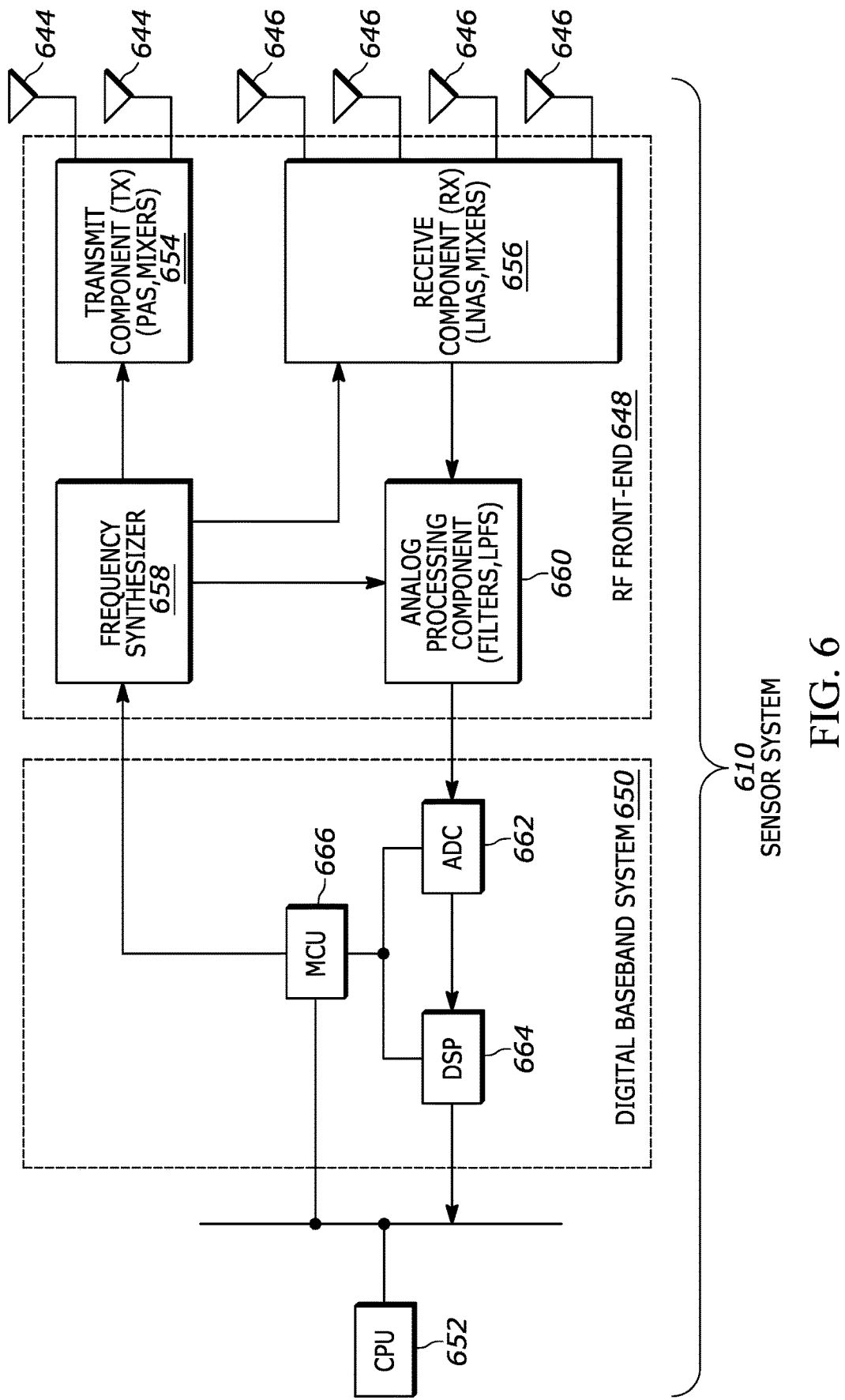
FIG. 6 depicts a functional block diagram of an embodiment of a sensor system that utilizes millimeter range radio waves.

FIG. 6 depicts a functional block diagram of an embodiment of a sensor system 610 that utilizes millimeter range radio waves to implement stepped frequency radar to implement operations such as ranging and imaging, including 2D or 3D imaging. The sensor system includes transmit (TX) antennas 644, receive (RX) antennas 646, an RF front-end 648, a digital baseband system 650, and a CPU 652. The components of the sensor system may be integrated together in various ways. For example, some combination of components may be fabricated on the same semiconductor substrate and/or included in the same packaged IC device or a combination of packaged IC devices. In an embodiment, the sensor system is designed to transmit and receive radio waves in the range of 2-6 GHz and/or in the range of 122-126 GHz. The sensor system may also operate in other frequency ranges, such as in a range around 24 GHz and/or in a range around 60 GHz.

In the embodiment of FIG. 6, the sensor system 610 includes two TX antennas 544 and four RX antennas 646. Although two TX and four RX antennas are used, there could be another number of antennas, e.g., one or more TX antennas and three or more RX antennas. In an embodiment, the RX antennas are configured in a 2D array. In an embodiment, the TX and RX antennas are configured to transmit and receive radio waves, respectively. For example, the antennas are configured to transmit and receive radio waves in the 2-6 GHz frequency range, e.g., wavelengths in the range of 149.89-49.96 mm and/or in the 122-126 GHz frequency range, e.g., wavelengths in the range of 2.46-2.38 mm.

In the embodiment of FIG. 6, the RF front-end 648 includes a transmit (TX) component 654, a receive (RX) component 656, a frequency synthesizer 658, and an analogue processing component 660. The transmit component may include elements such as power amplifiers (PAs) and mixers. The receive component may include elements such as low noise amplifiers (LNAs), variable gain amplifiers (VGAs), and mixers. The frequency synthesizer includes elements to generate electrical signals at frequencies that are used by the transmit and receive components. In an embodiment, the frequency synthesizer may include elements such as a crystal oscillator, a phase-locked loop (PLL), a frequency doubler, and/or a combination thereof. In an embodiment, the frequency synthesizer is digitally controlled by digital frequency control signals received from the digital baseband system. The analogue processing component may include elements such as mixers and filters, e.g., low pass filters (LPFs). In an embodiment, components of the RF front-end are implemented in hardware as electronic circuits that are fabricated on the same semiconductor substrate.

The digital baseband system 650 includes an analog-to-digital converter (ADC) 662, a digital signal processor (DSP) 664, and a microcontroller unit (MCU) 666. Although the digital baseband system is shown as including certain elements, the digital baseband system may include some other configuration, including some other combination of elements. The digital baseband system is connected to the CPU 652 via a bus.

Figure 7:
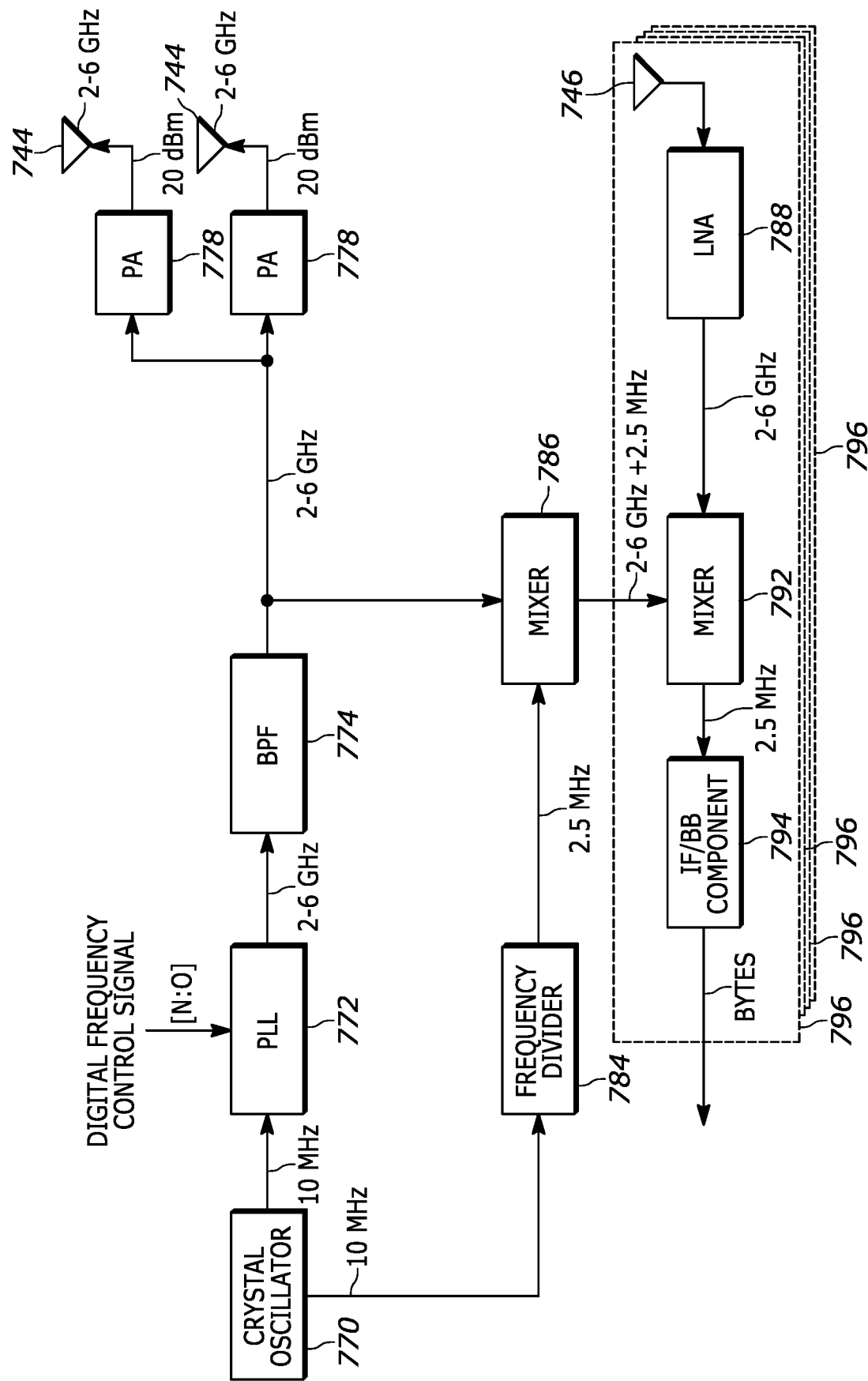
FIG. 7 depicts an expanded view of an embodiment of portions of the sensor system of FIG. 6, including elements of the RF front-end.

FIG. 7 depicts an expanded view of an embodiment of portions of the sensor system 610 of FIG. 6, including elements of the RF front-end 648 that are configured to operate in the 2-6 GHz frequency range. In the embodiment of FIG. 7, the elements include a crystal oscillator 770, a phase locked loop (PLL) 772 (e.g., a digitally controlled PLL), a bandpass filter (BPF) 774, power amplifiers (PAs) 778, TX antennas 744, a frequency divider 784, a mixer 786, an RX antenna 746, a low noise amplifier (LNA) 788, a mixer 792, and an Intermediate Frequency/Baseband (IF/BB) component 794. As illustrated in FIG. 7, the group of receive components identified within dashed box 796 is repeated four times, e.g., once for each of four distinct RX antennas.

Operation of the system shown in FIG. 7 is described with reference to a transmit operation and with reference to a receive operation. In an embodiment, stepped frequency scanning refers collectively to the transmit and receive operations. The description of a transmit operation generally corresponds to a left-to-right progression in FIG. 7 and description of a receive operation generally corresponds to a right-to-left progression in FIG. 7. With regard to the transmit operation, the crystal oscillator 770 generates an analog signal at a frequency of 10 MHz. The 10 MHz signal is provided to the PLL 772 and to the frequency divider 784. The PLL uses the 10 MHz signal to generate an analog signal that is in the 2-6 GHz frequency range. In an embodiment, the PLL is digitally controlled in response to digital frequency control signals (e.g., N bit control signals, where N is an integer of 1 or more) that set the desired output frequency of the PLL. The 2-6 GHz signal is provided to the BPF 774, which filters the input signal and passes a signal in the 2-6 GHz range to the PAs 778. The 2-6 GHz signal is also provided to the mixer 786.

The power amplifiers 778 amplify the RF signals in the 2-6 GHz range that are output from the TX antennas 744. In some embodiments, RF energy is transmitted from both antennas simultaneously and in other embodiments, RF energy is transmitted from only one TX antenna at a time, or from different subsets of TX antennas depending on how many TX antennas there are in the system. In an embodiment, the 2-6 GHz signals are output at 20 dBm (decibels (dB) with reference to 1 milliwatt (mW)). In an embodiment and as described below, the PLL 772 is digitally controlled to generate discrete frequency pulses between 2-6 GHz that are used for stepped frequency scanning. For example, as is described in more detail below, the 2-6 GHz frequency range can be divided into multiple distinct frequencies, e.g., up to 1,024 discrete frequencies that can be individually identified and selected through digital frequency control signals.

Dropping down in FIG. 7, the 10 MHz signal from the crystal oscillator 770 is also provided to the frequency divider 784, which divides the frequency down, e.g., from 10 MHz to 2.5 MHz via, for example, two divide by two operations, and provides an output signal at 2.5 MHz to the mixer 786. The mixer 786 also receives the 2-6 GHz signal from the BPF 774 and provides a signal at 2-6 GHz+2.5 MHz to the mixer 792 for receive signal processing.

With reference to a receive operation, electromagnetic (EM) energy is received at the RX antenna 746 and converted to electrical signals, e.g., voltage and current. For example, electromagnetic energy in the 2-6 GHz frequency band is converted to an electrical signal that corresponds in frequency (e.g., GHz), magnitude (e.g., power in dBm), and phase to the electromagnetic energy that is received at the RX antenna. The electrical signal is provided to the LNA 788. In an embodiment, the LNA amplifies signals in the 2-6 GHz frequency range and outputs an amplified 2-6 GHz signal. The amplified 2-6 GHz signal is then mixed with the 2-6 GHz+2.5 MHz signal at mixer 792 to generate a 2.5 MHz signal that corresponds to the electromagnetic energy that was received at the RX antenna. For example, when a 2 GHz signal is being transmitted from the TX antennas and received at the RX antenna, the mixer 792 receives a 2 GHz signal that corresponds to the electromagnetic energy that was received at the antenna and a 2 GHz+2.5 MHz signal from the mixer 786. The mixer 792 mixes the 2 GHz signal that corresponds to the electromagnetic energy that was received at the RX antenna with the 2 GHz+2.5 MHz signal from the mixer 786 to generate a 2.5 MHz signal that corresponds to the electromagnetic energy that was received at the RX antenna. The 2.5 MHz signal that corresponds to the electromagnetic energy that was received at the RX antenna is provided to the IF/BB component 794 for analog-to-digital conversion. The above-described receive process can be implemented in parallel on each of the four receive paths 796. As is described below, the system described with reference to FIG. 7 can be used to generate various discrete frequencies that can be used to implement, for example, stepped frequency radar detection, including stepped frequency radar ranging and stepped frequency radar imaging, e.g., 2D or 3D imaging. As described above, multiple mixing operations are performed to implement a sensor system as described herein. The multiple mixers and corresponding mixing operations implement a "compound mixing" architecture that enables use of such frequencies.

Figure 8:
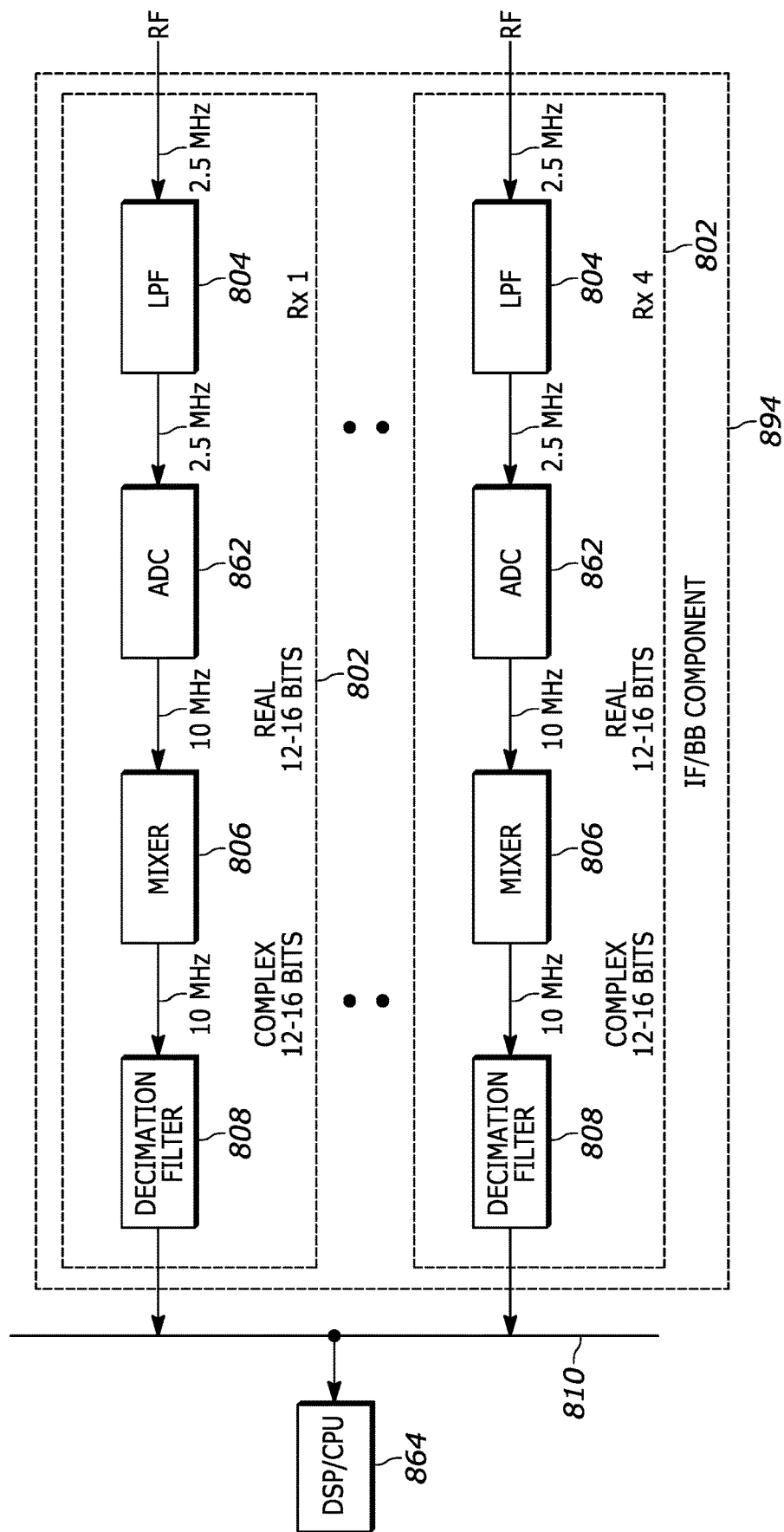
FIG. 8 depicts an embodiment of the IF/BB component shown in FIG. 7.

FIG. 8 depicts an embodiment of the IF/BB component 794 shown in FIG. 7. The IF/BB component 894 of FIG. 8 includes similar signal paths 802 for each of the four receive paths/RX antennas and each signal path includes a low pass filter (LPF) 804, an analog-to-digital converter (ADC) 862, a mixer 806, and a decimation filter 808. The operation of receive path 1, RX1, is described, although the description applies to each receive path.

As described above with reference to FIG. 7, the 2.5 MHz signal from mixer 792 (FIG. 7) is provided to the IF/BB component 794/894, in particular, to the LPF 804 of the IF/BB component 894. In an embodiment, the LPF filters the 2.5 MHz signal to remove negative frequency spectrum and noise outside of the desired bandwidth. After passing through the LPF, the 2.5 MHz signal is provided to the ADC 862, which converts the 2.5 MHz signal (e.g., IF signal) to digital data at a sampling rate of 10 MHz (e.g., as 12-16 bits of "real" data). The mixer 806 multiplies the digital data with a complex vector to generate a digital signal (e.g., 12-16 bits of "complex" data), which is also sampled at 10 MHz. Although the signal is sampled at 10 MHz, other sampling rates are possible, e.g., 20 MHz. The digital data sampled at 10 MHz is provided to the decimation filter 808, which is used to reduce the amount of data by selectively discarding a portion of the sampled data. For example, the decimation filter reduces the amount of data by reducing the sampling rate and getting rid of a certain percentage of the samples, such that fewer samples are retained. The reduction in sample retention can be represented by a decimation factor, M, and may be, for example, about 10 or 100 depending on the application, where M equals the input sample rate divided by the output sample rate.

The output of the decimation filter 806 is digital data that is representative of the electromagnetic energy (e.g., in frequency, amplitude, and/or phase) that was received at the corresponding RX antenna. In an embodiment, samples are output from the IF/BB component 894 at rate of 1 MHz (using a decimation factor of 10) or at a rate of 100 kHz (using a decimation factor of 100). The digital data is provided to a DSP and/or CPU 864 via a bus 810 for further processing. For example, the digital data is processed to perform ranging and/or imaging, which may involve isolating a signal from a particular location, e.g., isolating signals that correspond to electromagnetic energy that was reflected from a particular object (e.g., a person or a weapon carried by a person). In an embodiment, stepped frequency scanning across a frequency range includes the processes of transmitting stepped frequency pulses at discrete frequencies, receiving RF energy, and outputting corresponding digital data. Stepped frequency scanning may also include processing of the generated digital data to generate ranging information, imaging information, and/or some intermediate information. In an embodiment, signal processing techniques may be applied to implement beamforming, Doppler effect processing, and/or leakage mitigation to isolate a desired signal from other undesired signals.

In conventional RF systems, the analog-to-digital conversion process involves a high direct current (DC), such that the I ("real") and Q ("complex") components of the RF signal at DC are lost at the ADC. Using the system as described above with reference to FIGS. 6-8, the intermediate frequency, IF, is not baseband, so I and Q can be obtained after analog-to-digital conversion and digital mixing as shown in FIG. 8.

In an embodiment, certain components of the sensor system are integrated onto a single semiconductor substrate and/or onto a single packaged IC device (e.g., a packaged IC device that includes multiple different semiconductor substrates (e.g., different die) and antennas). For example, elements such as the components of the RF front-end 648, and/or components of the digital baseband system 650 (FIGS. 6-8) are integrated onto the same semiconductor substrate (e.g., the same die). In an embodiment, components of the sensor system are integrated onto a single semiconductor substrate that is approximately 5 mm×5 mm.

In an embodiment, digital signal processing of the received signals may involve implementing Kalman filters to smooth out noisy data. In another embodiment, digital signal processing of the received signals may involve combining receive chains digitally. Other digital signal processing may be used to implement beamforming, Doppler effect processing, and ranging. Digital signal processing may be implemented in a DSP and/or in a CPU.

Figure 9:
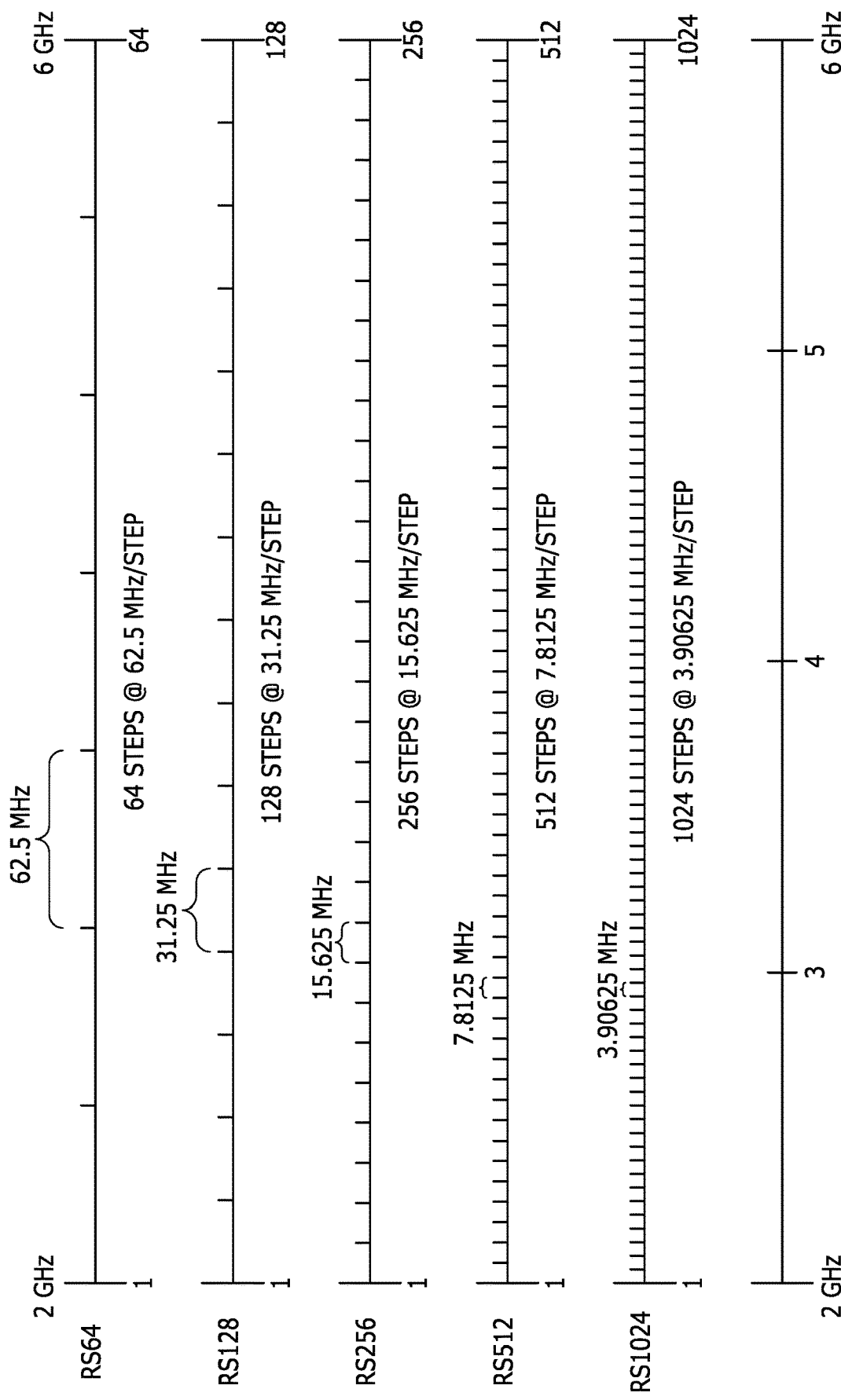
FIG. 9 illustrates the frequency range of 2-6 GHz relative to different range scales.

As described above with reference to FIGS. 6 and 7, the frequency synthesizer (FIG. 6, 658) of the RF front-end (FIG. 6, 648) can generate discrete frequencies for transmission as frequency pulses (also referred to as discrete frequency pulses) in response to digital frequency control signals received from the digital baseband system (FIG. 6, 650). In an embodiment, the addressable frequency range of the sensor system is divided into a number of individually addressable discrete frequencies. For example, the addressable frequency range of 2-6 GHz is divided into 64, 128, 256, 512, or 1,024 individually addressable discrete frequencies. The number of individually addressable discrete frequencies in turn determines the step size (or vice versa), such that 64 discrete frequencies in the 2-6 GHz frequency range corresponds to a step size of 62.5 MHz/step (4 GHz/64=62.5 MHz). Thus, as used herein the term "range scale" or "RS" refers to the number of individually/digitally addressable frequencies that can be generated using digital frequency control signals. That is, the range scale (RS) is the scale at which the digitally addressable frequency range is divided. FIG. 9 illustrates the frequency range of 2-6 GHz relative to range scales of RS64, RS128, RS256, RS512, and RS1024. In the example illustrated in FIG. 9, for the frequency range of 2-6 GHz, the example range scales and corresponding step sizes are:

RS64=64 total steps at 62.5 MHz/step;
RS128=128 total steps at 31.25 MHz/step;
RS256=256 total steps at 15.625 MHz/step;
RS512=512 total steps at 7.8125 MHz/step; and
RS1024=1,024 total steps at 3.90625 MHz/step.

Using the approach illustrated in FIG. 9, each discrete frequency is individually and uniquely identifiable by a number (e.g., which can be communicated as a digital signal in binary form) depending on the range scale. For example, the frequencies of 2 GHz, 3 GHz, 4 GHz, 5 GHz, and 6 GHz can be individually identified by the respective numeric values depending on the range scale:

1/16/32/48/64 at RS64;
1/32/64/96/128 at RS128;
1/64/128/192/256 at RS256;
1/128/256/384/512 at RS512; and
1/256/512/768/1024 at RS1024.

Figure 10:
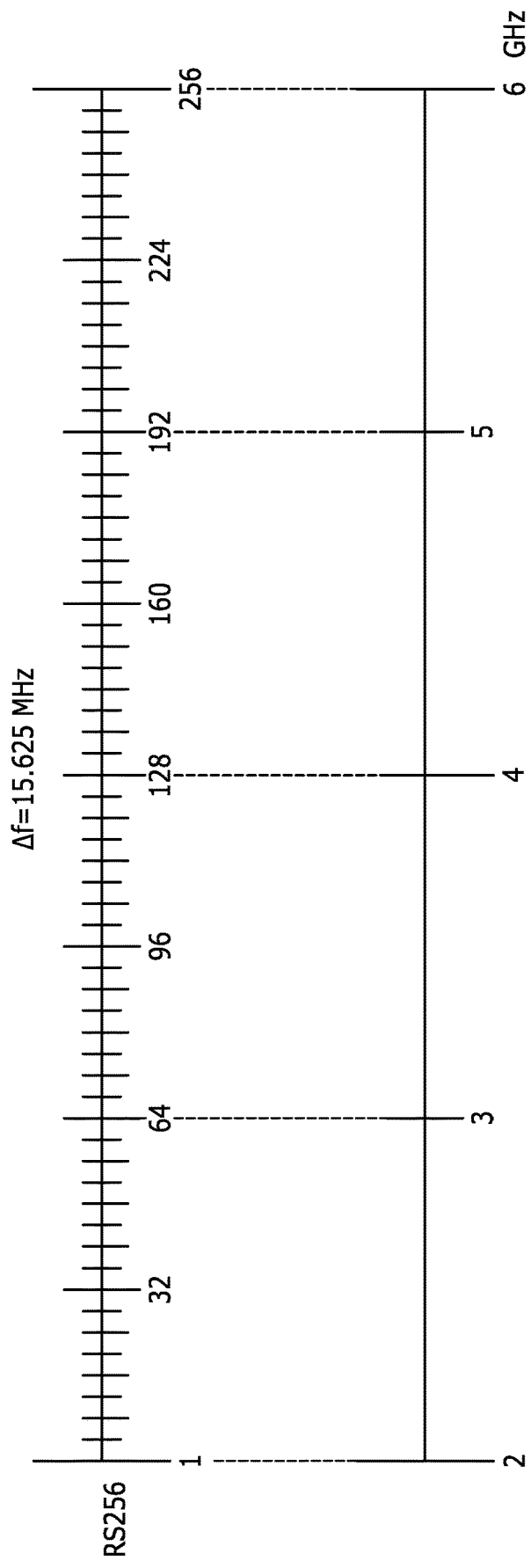
FIG. 10 depicts the frequency range of 2-6 GHz relative to a range scale of 256.

To further illustrate how numeric values can be used to individually identify discrete frequencies for use in stepped frequency radar, FIG. 10 depicts the frequency range of 2-6 GHz relative to a range scale of 256 (RS256). As illustrated in FIG. 10, numeric value "1" corresponds to 2 GHz, numeric value "64" corresponds to 3 GHz, numeric value "128" corresponds to 4 GHz, numeric value "192" corresponds to 5 GHz, and numeric value "256" corresponds to 6 GHz. Using the above-described approach to identify discrete frequencies, step sizes can be generated as multiples of the step size of the particular range scale (RS). For example, at RS64, it is possible to digitally identify discrete frequency steps at multiples of 62.5 MHz/step, whereas at RS256, it is possible to digitally identify discrete frequency steps at multiples of 15.625 MHz (e.g., 15.625 MHz/step, 31.25 MHz/step, or 62.5 MHz/step), at RS512, it is possible to digitally identify discrete frequency steps at multiples of 7.8125 MHz (e.g., 7.8125 MHz, 15.625 MHz/step, 31.25 MHz/step, or 62.5 MHz/step), and at RS1024, it is possible to digitally identify discrete frequency steps at multiples of 3.90625 MHz (e.g., 3.90625 MHz, 7.8125 MHz, 15.625 MHz/step, 31.25 MHz/step, or 62.5 MHz/step). In an embodiment, a single range scale (RS) is used to digitally identify a wide range of discrete frequencies and a wide range of step sizes. For example, the range scale 1,024 (RS1024) is used to digitally identify a wide range of discrete frequencies and a wide range of step sizes. Examples of using digital frequency control signals to implement stepped frequency scanning in a stepped frequency radar system are described below.

Figure 11:
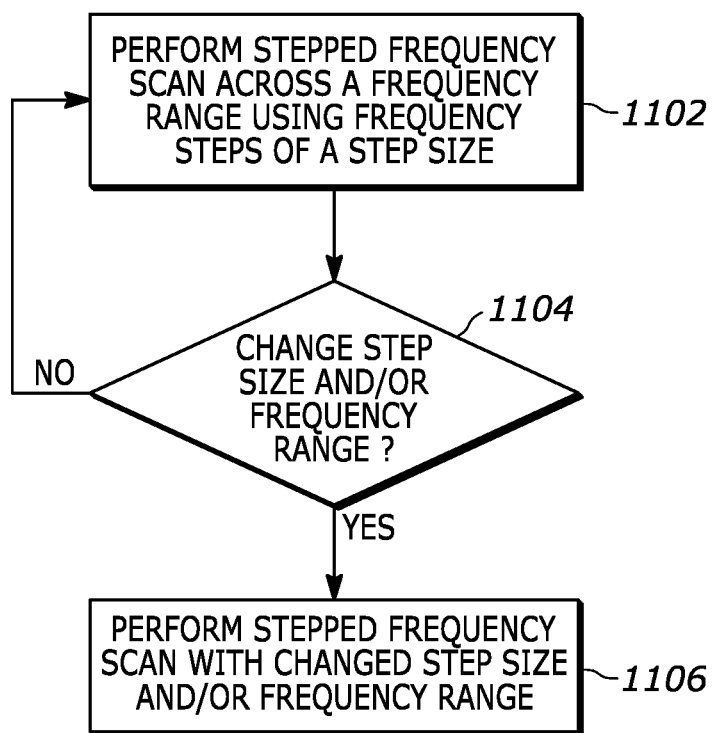
FIG. 11 is a process flow diagram of operation of stepped frequency radar scanning.

In accordance with an embodiment of the invention, the step size and/or frequency range of stepped frequency scanning is changed during a scanning operation. For example, the step size is changed from a first step size to a second step size and/or the frequency range that is scanned is changed from a first frequency range to a second frequency range. FIG. 11 is a process flow diagram of operation of stepped frequency radar scanning. At block 1102, stepped frequency scanning is performed across a frequency range using frequency steps of a step size. At decision point 1104, it is determined whether or not the step size and/or the frequency range should be changed. Various criteria can be used to determine if and when the step size and/or frequency range should be changed. If at decision point 1104 it is determined that the step size and/or frequency range should not be changed, then the process returns to block 1102. If on the other hand, it is determined that the step size and/or frequency range should be changed, then the process proceeds to block 1106. At block 1106, stepped frequency scanning is performed with the changed step size and/or frequency range. In an embodiment, the frequency of the transmitted frequency pulses and the step sizes are controlled by digital frequency control signals and changes to the step size and/or frequency range are made based on preprogrammed digital frequency control signals and in other embodiments, changes to the step size and/or frequency range are made in response to feedback information from the received signals.

Figure 12:
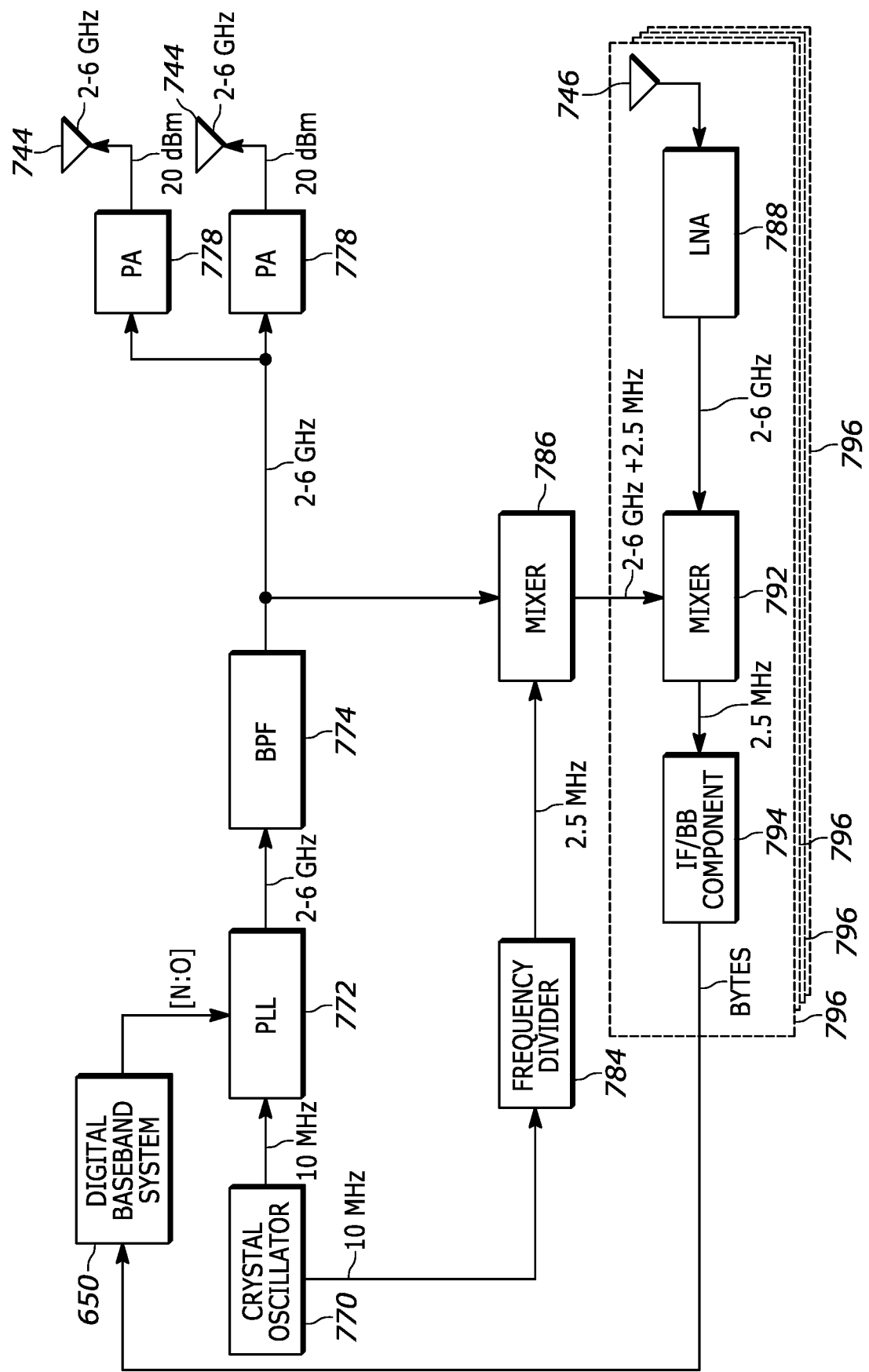
FIG. 12 depicts a feedback loop between the transmit and receive elements of the sensor system described with reference to FIGS. 6 and 7.

In an embodiment, at least one parameter of the stepped frequency scanning is changed in response to feedback information from the received signals of the stepped frequency scanning. For example, the step size and/or scanned frequency range may be changed in response to identifying an object or in response to an indication that an object may be present. FIG. 12 depicts a feedback loop between the transmit and receive elements of the sensor system described above with reference to FIGS. 6-8. In particular, the sensor system depicted in FIG. 12 is the same as the sensor system depicted in FIG. 7 except that the sensor system depicted in FIG. 12 includes the digital baseband system 650 and a feedback loop that is formed by the digital output of the IF/BB component 794 of the RF front-end, the digital baseband system 650, and digital frequency control signals that are provided to the PLL 772 from the digital baseband system 650. Using the feedback loop illustrated in FIG. 12, the discrete frequencies that are generated by the PLL can be digitally controlled by the digital baseband system in response to an evaluation of digital data received from the IF/BB component 794 of the RF front-end. The particular logic used to evaluate the received digital data and to change the step size and/or frequency range can be dependent on many factors, including the particular application in which the sensor system is deployed. Some examples of logic associated with changing the step size and/or frequency range are described below. Although FIG. 12 illustrates a feedback based control scheme, in other embodiments, the step size and/or frequency range of the stepped frequency scanning can be changed according to preprogrammed frequency control signals and/or pre-established rules.

As described above, digital control of discrete frequencies in stepped frequency radar scanning enables flexible scanning that can be adapted to implement various features and/or to achieve various goals. At frequencies in the 2-6 GHz range, larger step sizes may be more effective for ranging (i.e., determining the range of an object) and smaller step sizes may be more effective for imaging (i.e., determining the dimensions of an object, particularly in 2D, e.g., relative to a plane that is perpendicular to a line between the sensor system and the object). Thus, in one application, it may be desirable to identify the range of an object using frequency pulses transmitted at a first step size and to identify a 2D or 3D profile of the object or a related object using frequency pulses transmitted at a second, smaller, step size, and possibly at a third, even smaller, step size. For example, in a security sensor application, it may be desirable to use frequency pulses transmitted over a wide frequency range at a first step size to identify the range of an object (e.g., a person and/or a weapon) and then use frequency pulses transmitted over a narrower frequency range at a second, smaller, step size to identify the 2D or 3D profile of an object (e.g., a person and/or a weapon carried by the person). In an embodiment, the particular step sizes and/or frequency ranges are selected/changed/adjusted in real time based on feedback from the received signals (e.g., "on-the-fly" adjustment). For example, the step sizes and/or frequency ranges can be changed on-the-fly in a couple of repetition intervals, T. The received signals may change as different frequencies reflect off different objects in different ways (e.g., some frequencies will resonate from a weapon better than other frequencies) and therefore the parameters of the stepped frequency scanning can be adapted on the fly to the current conditions that are being experienced. In an embodiment, smaller step sizes around a specific narrower frequency range may be better suited for 2D or 3D imaging of an object such as a weapon due to the relatively high reflectivity of portions of a weapon (e.g., around a particular frequency range) that tend to be smooth, such as the barrel. Alternatively, parameters (e.g., step size and frequency range (frequency range could refer to the difference between two frequencies or frequency range could refer to a specific frequency range that is defined by two absolute frequencies)) of the stepped frequency scanning can be pre-programmed.

Figure 13A:
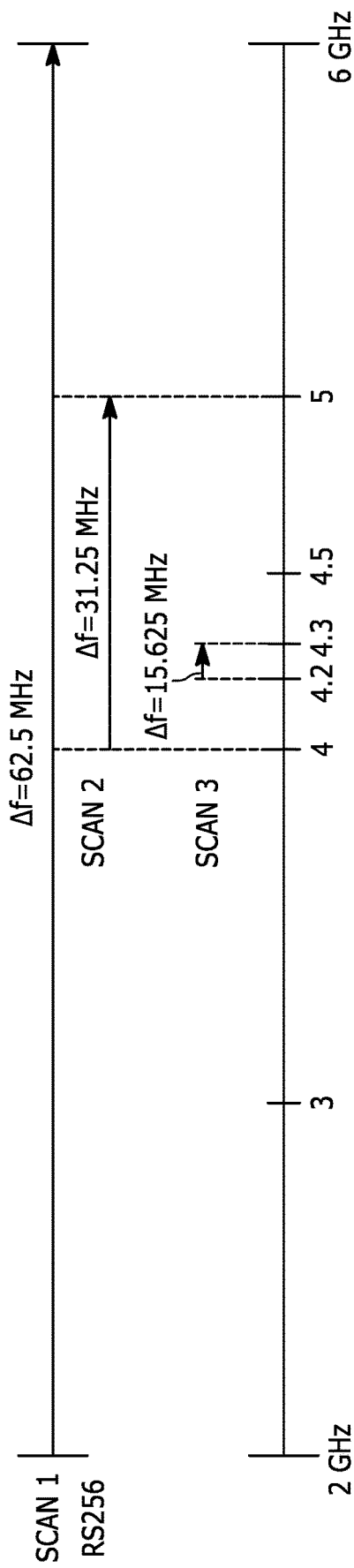
FIGS. 13A and 13B illustrate two different examples of a scanning operation, which involves scanning a relatively wide frequency range at a first step size and scanning a more narrow frequency range at a smaller step size or step sizes.
Figure 13B:
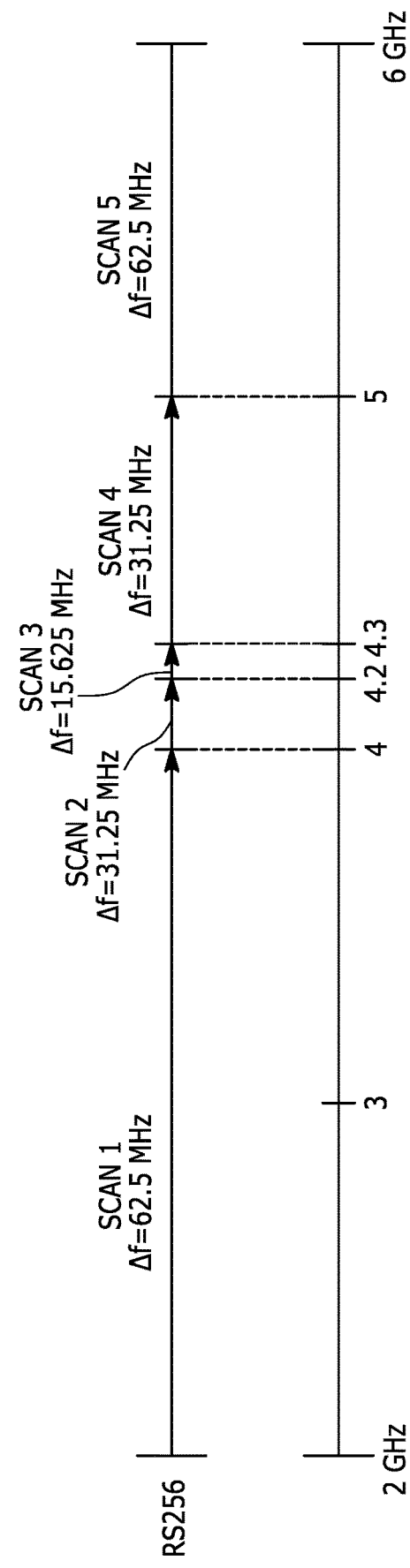

FIGS. 13A and 13B illustrate two different examples of a stepped frequency scanning operation, referred to as a "telescopic," "zoom," or "focused" stepped frequency scanning operation, which involves scanning a relatively wide frequency range at a first step size and scanning a more narrow frequency range (or frequency ranges) at a smaller step size or step sizes. The example illustrated in FIG. 13A is referred to as an "overlapping" stepped frequency scanning operation and the example illustrated in FIG. 13B is referred to as a "non-overlapping" stepped frequency operation.

With reference to FIG. 13A, a first scan (scan 1) of the frequency range of 2-6 GHz is performed at a step size of 62.5 MHz ($\Delta f=62.5$ MHz), a second scan (scan 2) of the frequency range of 4-5 GHz is performed at a step size of 31.25 MHz ($\Delta f=31.25$ MHz), and then a third scan (scan 3) of the frequency range of approximately 4.2-4.3 GHz is performed at a step size of 15.625 MHz ($\Delta f=15.625$ MHz). As illustrated in FIG. 13A, scans 1, 2, and 3 each separately scan the frequency range of 4.2-4.3 GHz and thus the three scans "overlap" in the 4.2-4.3 GHz frequency range.

With reference to FIG. 13B, a first scan (scan 1) of the frequency range of 2-4 GHz is performed at a step size of 62.5 MHz ($\Delta f=62.5$ MHz), a second scan (scan 2) of the frequency range of 4-5 GHz is performed at a step size of 31.25 MHz ($\Delta f=31.25$ MHz), a third scan (scan 3) of the frequency range of approximately 4.2-4.3 GHz is performed at a step size of 15.625 MHz ($\Delta f=15.625$ MHz), a fourth scan (scan 4) of the frequency range of 4.3-5 GHz is performed at a step size of 31.25 MHz ($\Delta f=31.25$ MHz), and then a fifth scan (scan 5) of the frequency range of 5-6 GHz is performed at a step size of 62.5 MHz ($\Delta f=62.5$ MHz). As illustrated in FIG. 13B, scans 1, 2, 3, 4, and 5 all scan over different, non-overlapping, frequency ranges and thus are "non-overlapping" over the range of 2-6 GHz.

In an embodiment, when using the sensor system for a security application that involves identifying weapons such as handguns, rifles, and knives, including weapons carried by a person, the stepped frequency scanning may implement some form of the above-described "telescopic," "zoom," or "focused" stepped frequency scanning when the reflected signals indicate that a more reflective object (e.g., a smooth object) is within range of the sensor system. In one embodiment, an increase in the magnitude of RF energy at certain wavelengths that correspond to known sizes of weapons such as handguns, rifles, and knives (e.g., due to such frequencies resonating off the weapon), may indicate that such an object is within range of the sensor system. Therefore, in an embodiment, the step size to be used in stepped frequency scanning and the frequency range to be scanned are adjusted when certain reflective characteristics are detected. In one embodiment, the frequency range is reduced to a frequency range more closely focused on a frequency range of interest (e.g., a frequency range that is known through training to correspond to resonant wavelengths of a weapon) and the step size is reduced to a step size that can produce 2D profile information that can be used to determine (e.g., to some degree of certainty) if a weapon may be present. In an embodiment, in a security sensor application, it may be desirable to use frequency pulses transmitted at a first step size to identify the range of an object (e.g., a person and/or a weapon) and upon receiving RF energy that indicates a person is present or that an object that may be weapon is present, the sensor system changes on the fly to transmitting frequency pulses at a second, smaller, step size over a narrower frequency range (e.g., around frequencies that are known to resonate from a weapon such as a handgun, rifle, or knife) to identify the 2D or 3D profile of an object (e.g., a person and/or a weapon). In an embodiment, the particular step sizes and/or frequency ranges are selected/changed/adjusted in real time in response to information received via the feedback loop of the sensor system as described with reference to FIG. 12.

Figure 14A:
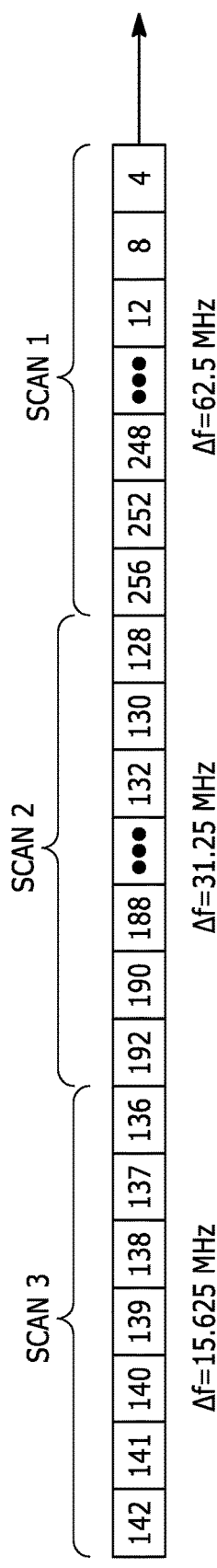
FIGS. 14A and 14B illustrate digital frequency control signals that correspond to the stepped frequency scanning operations illustrated in FIGS. 13A and 13B, respectively.
Figure 14B:
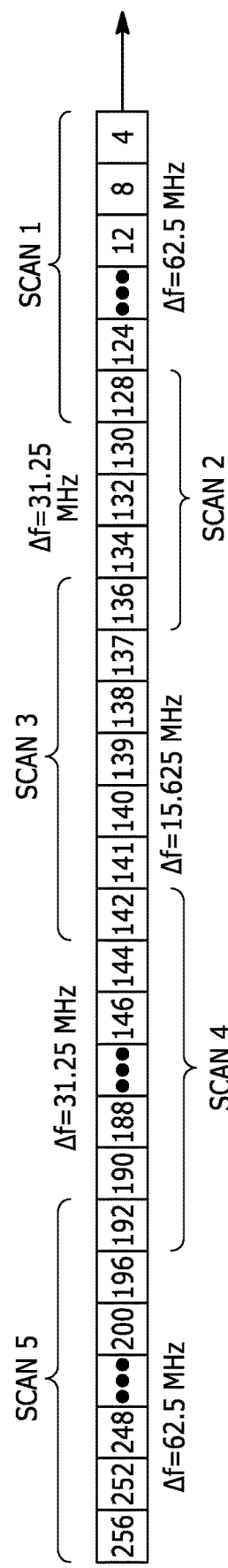

As described above with reference to FIGS. 9 and 10, the individually addressable discrete frequencies used in the stepped frequency scanning can be controlled by digital frequency control signals. FIGS. 14A and 14B illustrate digital frequency control signals that correspond to the stepped frequency scanning operations illustrated in FIGS. 13A and 13B, respectively. In the examples of FIGS. 14A and 14B, a range scale of 256, RS256, is used as the range scale to identify the individually addressable discrete frequencies that are transmitted from the sensor system. With reference to FIG. 14A (which corresponds to FIG. 13A), the discrete frequencies of scans 1, 2, and 3 are identified in a sequential (in time) stream of numeric frequency identifiers. Using an RS256 notation, discrete frequencies 4, 8, 12, . . . , 248, 252, and 256 are generated and transmitted as frequency pulses to implement scan 1 at a step size of $\Delta f=62.5$ MHz. Next, discrete frequencies 128, 130, 132, . . . , 188, 190, and 192 are generated and transmitted as frequency pulses to implement scan 2 at a step size of $\Delta f=31.25$ MHz. Lastly, discrete frequencies 136, 137, 138, 139, 140, 141, and 142 are generated and transmitted as frequency pulses to implement scan 3 at a step size of $\Delta f=15.625$ MHz.

With reference to FIG. 14B (which corresponds to FIG. 13B), the discrete frequencies of scans 1, 2, 3, 4, and 5 are identified in a sequential (in time) stream of numeric frequency identifiers. Using an RS256 notation, discrete frequencies 4, 8, 12, . . . , 124, and 128 are generated and transmitted as frequency pulses to implement scan 1 at a step size of $\Delta f=62.5$ MHz. Next, discrete frequencies 128, 130, 132, 134, and 136 are generated and transmitted as frequency pulses to implement scan 2 at a step size of $\Delta f=31.25$ MHz. Next, discrete frequencies 136, 137, 138, 139, 140, 141, and 142 are generated and transmitted as frequency pulses to implement scan 3 at a step size of $\Delta f=15.625$ MHz. Next, discrete frequencies 142, 144, 146, . . . , 188, 190, and 192 are generated and transmitted as frequency pulses to implement scan 4 at a step size of $\Delta f=31.25$ MHz. Lastly, discrete frequencies 192, 196, 200, . . . , 248, 252, and 256 are generated and transmitted as frequency pulses to implement scan 5 at a step size of $\Delta f=62.5$ MHz. As illustrated in FIGS. 13A-14B, digital control of discrete frequencies in a stepped frequency radar system enables "telescopic," "zoom," or "focused" stepped frequency scanning to transmit frequency pulses at a first step size to identify the range of an object (e.g., a person and/or a weapon) and then to change the step size and scanned frequency range on the fly to a smaller step size over a narrower frequency range (e.g., around frequencies that are known to resonate from a weapon such as a handgun, rifle, or knife) to identify the 2D or 3D profile of an object (e.g., a person and/or a weapon).

Figure 15A:
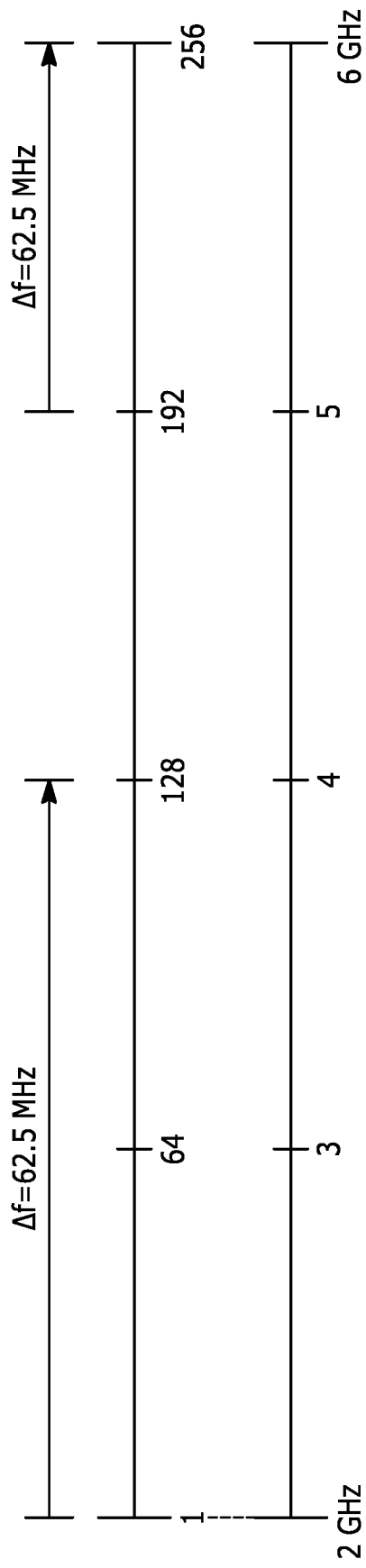
FIG. 15A illustrates an example of frequency hopping in a stepped frequency scanning operation.

As described above, digital control of discrete frequencies in stepped frequency radar scanning enables flexible scanning that can be adapted to implement various features and/or to achieve various goals. In some cases, it may be desirable to skip or "hop" a particular frequency band to, for example, avoid a frequency band that may experience interfering RF energy. FIG. 15A illustrates an example of "frequency hopping" in a stepped frequency scanning operation relative to the 2-6 GHz frequency range and a range scale of 256 (RS256). In the example of FIG. 15A, stepped frequency scanning is performed over a frequency range of 2-6 GHz at step size of 62.5 MHz, $\Delta f=62.5$ MHz, with the frequency band of 4-5 GHz being skipped or "hopped" over. In a stepped frequency scanning operation, the frequency range of 2-4 GHz is scanned at 62.5 MHz steps and then the frequency range of 5-6 GHz is scanned at 62.5 MHz steps. In an embodiment, the stepped frequency scanning is performed at the same sweep rate throughout the scan. That is, the time between frequency steps is constant (e.g., interval, T, see FIGS. 2, 3B, 4A, and 3B) even through the frequency hop.

Figure 15B:
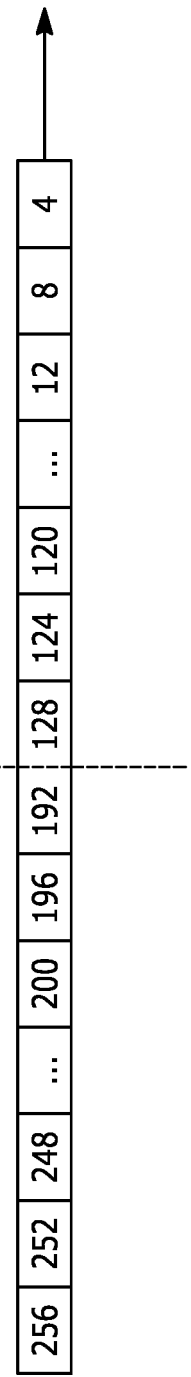
FIG. 15B illustrates digital frequency control signals that correspond to the frequency hopping operation illustrated in FIG. 15A.

As described above with reference to FIGS. 9, 10, 14A, and 14B, the discrete frequencies used in the stepped frequency scanning can be controlled by digital frequency control signals. FIG. 15B illustrates digital frequency control signals that correspond to the stepped frequency scanning operation illustrated in FIG. 15A. In the example of FIG. 15B, a range scale of 256, RS256, is used as the range scale to identify discrete frequencies and the discrete frequencies of the scan are identified in a sequential (in time) stream of numeric frequency identifiers. Using an RS256 notation, discrete frequencies 4, 8, 12, . . . , 120, 124, and 128 are generated and corresponding frequency pulses are transmitted to implement the scan of the 2-4 GHz frequency range at a step size of $\Delta f=62.5$ MHz and discrete frequencies 192, 196, 200, . . . , 248, 252, and 256 are generated and corresponding frequency pulses are transmitted to implement the scan of the 5-6 GHz frequency range at a step size of $\Delta f=62.5$ MHz. In the example of FIG. 15B, the digitally controlled frequency hop is indicated by a dashed vertical line, which indicates where the digital frequency control signals jump from numeric value 128 to 192 in one step. Although the numeric values of the digital frequency control signals jump from numeric value 128 to 192, the jump happens in one step (e.g., one fixed time interval, T) so that there is no added time gap associated with the frequency hop.

Figure 16:
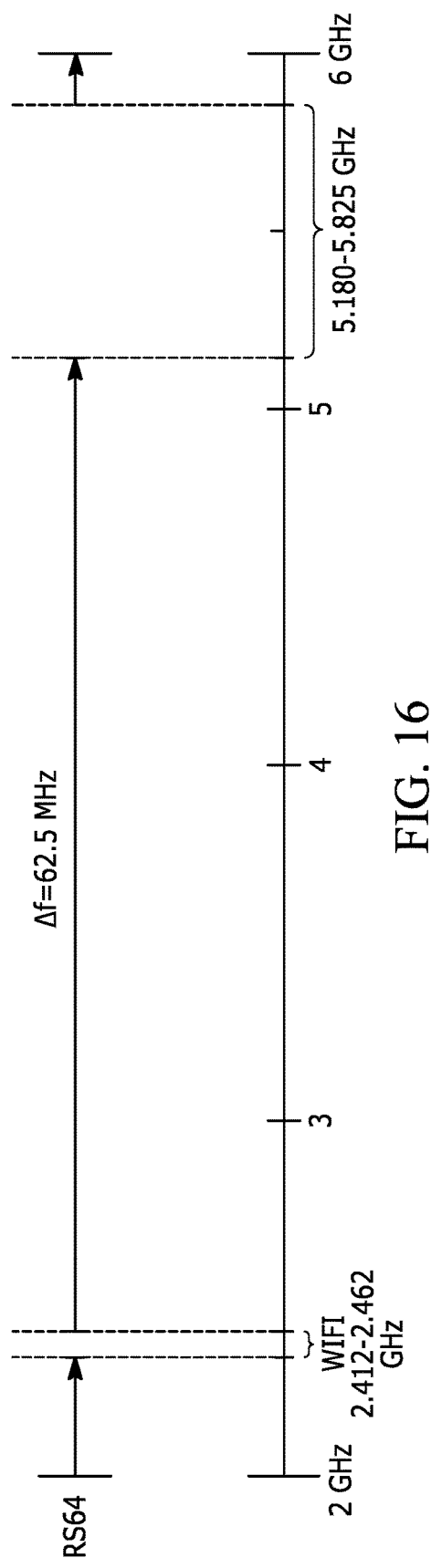
FIG. 16 illustrates an example of a case in which frequency hopping is implemented in stepped frequency radar to avoid frequency bands of known interference.

The concept of frequency hopping in stepped frequency radar operations is described above with reference to FIGS. 15A and 15B. In environments that implement a wireless communications protocol such as WIFI, the frequency bands of 2.412-2.462 GHz and 5.180-5.825 GHz may include RF energy that could interfere with the sensor system described herein. Therefore, in an embodiment, stepped frequency radar scanning can be performed in a manner that "hops over" known interfering frequency bands, e.g., the interfering frequency bands of 2.412-2.462 GHz and 5.180-5.825 GHz. FIG. 16 illustrates an example of a case in which frequency hopping is implemented in stepped frequency radar using digital frequency control signals to avoid frequency bands of known interference. Specifically, the example of FIG. 16 illustrates frequency hopping over the WIFI frequency bands of 2.412-2.462 GHz and 5.180-5.825 GHz, although the techniques can be applied to other known interfering frequency bands.

Figure 17:
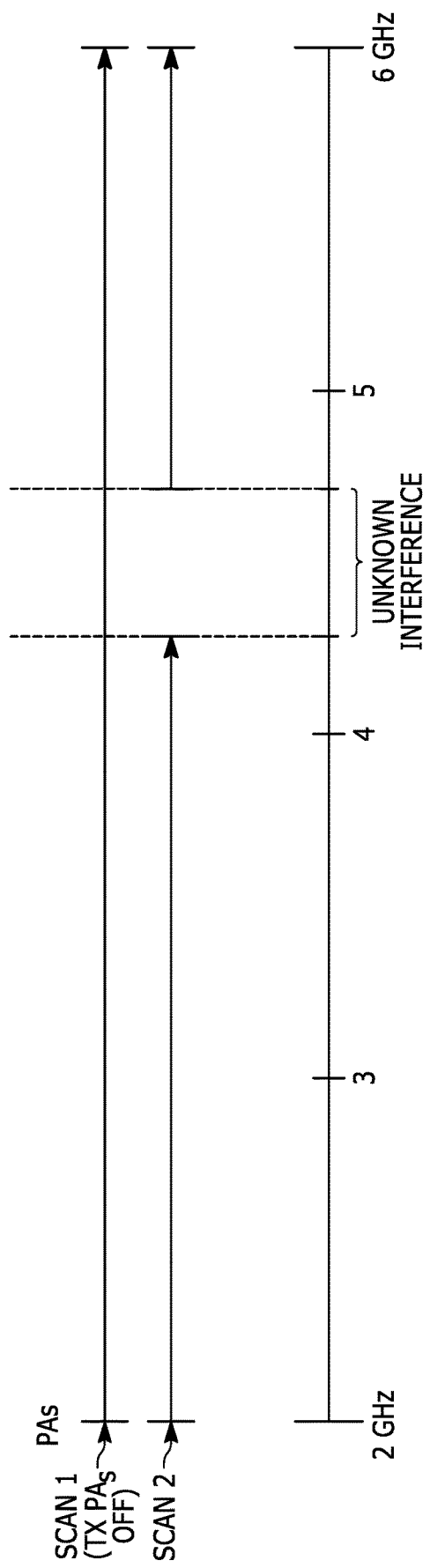
FIG. 17 illustrates a process in which a frequency range is first scanned to identify an interfering frequency band and then the subsequent scan is controlled to hop over the identified interfering frequency band.

In the example described with reference to FIG. 16, the WIFI frequency bands of 2.412-2.462 GHz and 5.180-5.825 GHz are known. However, in other applications, the existence of interfering RF energy in the surrounding environment may not be known. Thus, in an embodiment, the existence of interfering RF energy in the surrounding environment is learned by the sensor system and then the sensor system can adapt the stepped frequency scanning to hop over frequency bands that are identified to exhibit RF energy that may interfere with stepped frequency radar operations. FIG. 17 illustrates a process in which a frequency range is first scanned to identify an interfering frequency band and then the subsequent scan (or scans) hops over the identified interfering frequency band. In an embodiment and as illustrated in FIG. 17, first, a learning scan (scan 1) is performed over the entire addressable frequency range, e.g., 2-6 GHz. In an embodiment, the learning scan is performed with the transmitter PAs deactivated (e.g., the PAs 678 in the sensor system depicted in FIG. 6 turned off or otherwise bypassed) and the sensor system scanning the 2-6 GHz frequency range for interfering signals. For example, with reference to FIG. 7, the PLL generates discrete frequency pulses in a stepped frequency manner and the frequency pulses are distributed throughout sensor system as described with reference to FIG. 7 except that amplified frequency pulses are not transmitted from the TX antennas because the PAs are deactivated. In the example of FIG. 7, it is assumed that interfering RF energy is found in the approximately 4.3-4.6 GHz frequency band and so the stepped frequency scanning is digitally controlled to hop over the 4.3-4.6 GHz frequency band. In scan 2, the sensor system is digitally controlled to hop over the interfering frequency band using the techniques described above with reference to FIGS. 15A and 15B.

Figure 18A:
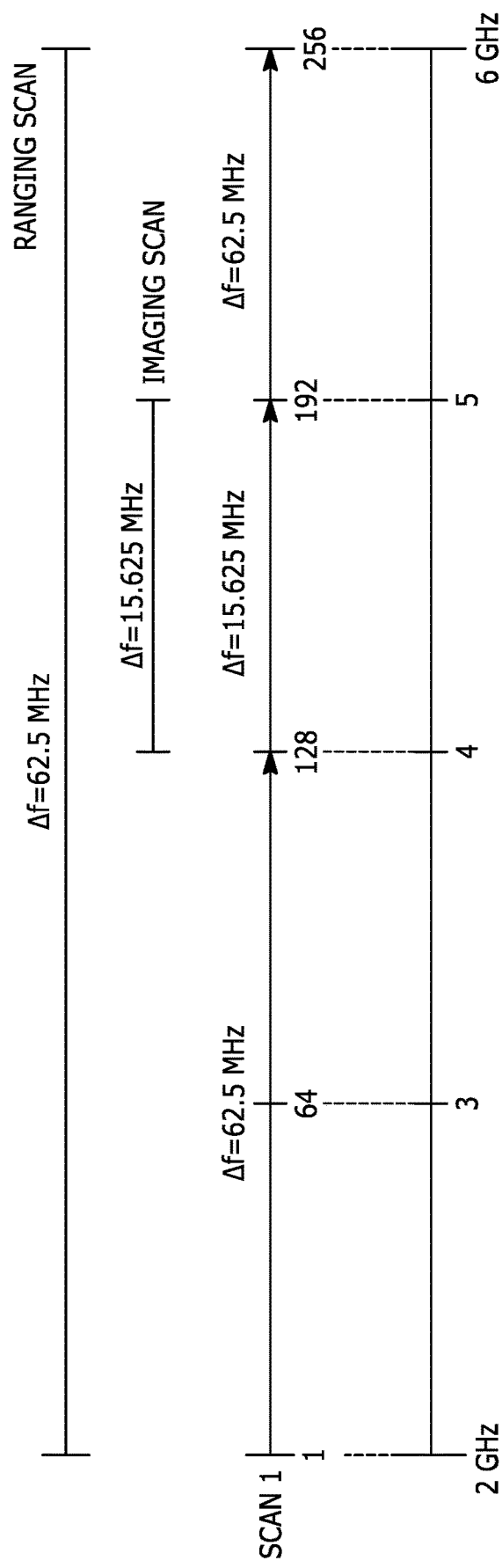
FIG. 18A illustrates stepped frequency scanning over the 2-6 GHz frequency range in which ranging scanning is performed over the entire 2-6 GHz frequency range simultaneously with imaging scanning that is performed over only the 4-5 GHz frequency range.

It has been found that larger frequency steps can be better for ranging and smaller frequency steps can be better for 2D or 3D imaging of certain objects of interest such as humans and weapons such as handguns, rifles, and knives. However, performing separate stepped frequency scans for ranging and imaging takes additional time. Therefore, in an embodiment, stepped frequency scanning is performed to simultaneously implement stepped frequency scanning for two different purposes, e.g., for "ranging scanning" and for "imaging scanning," which enables the generation of both ranging data and imaging data. FIG. 18A illustrates stepped frequency scanning over the 2-6 GHz frequency range in which ranging scanning is performed over the entire 2-6 GHz frequency range simultaneously with imaging scanning that is performed over only the 4-5 GHz frequency range. In particular, in the example of FIG. 18A, ranging scanning is performed at a first step size, e.g., $\Delta f=62.5$ MHz, and imaging scanning is performed at a second, smaller, step size, e.g., $\Delta f=15.625$ MHz. In order to perform simultaneous ranging scanning and imaging scanning, in an embodiment, over the frequency range of 2-4 GHz, discrete frequencies are stepped at 62.5 MHz/step, then over the frequency range of 4-5 GHz, discrete frequencies are stepped at 15.625 MHz/step, and then over the frequency range of 5-6 GHz, discrete frequencies are stepped again at 62.5 MHz/step. As illustrated in FIG. 18A, a single non-overlapping scan across the frequency range of 2-6 GHz includes frequency bands that are scanned at different step sizes.

Figure 18B:
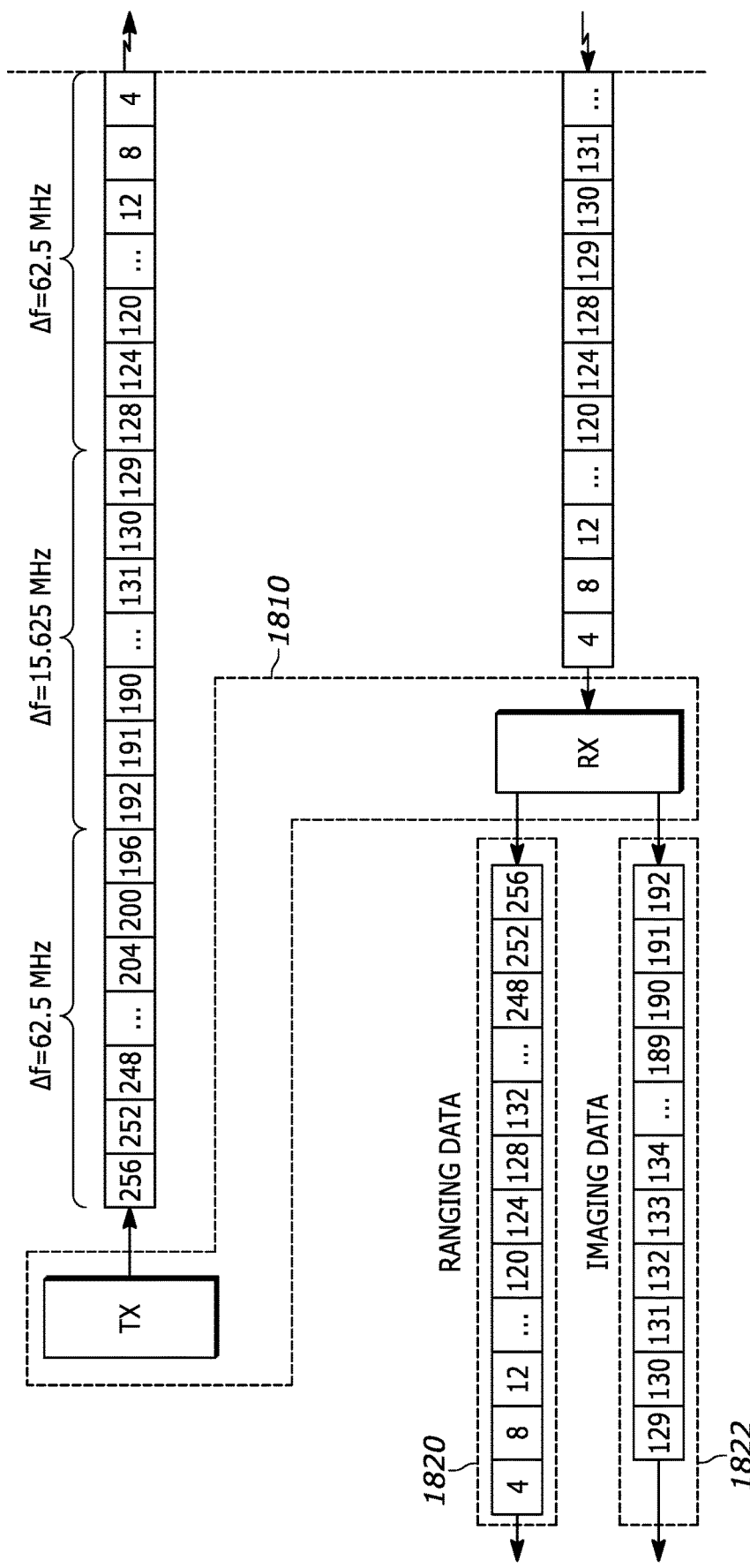
FIG. 18B illustrates digital frequency coding for the stepped frequency scanning illustrated in FIG. 18A.

FIG. 18B illustrates digital frequency coding (in a time sequence) for the stepped frequency scanning illustrated in FIG. 18A. At the transmitter (TX), discrete frequencies are stepped at 62.5 MHz/step, then discrete frequencies are stepped at 15.625 MHz/step, then discrete frequencies are stepped at 62.5 MHz/step. The digital frequency coding using an RS256 scale includes a first scan segment of frequencies 4, 8, 12, . . . , 120, 134, and 128 ($\Delta f=62.5$ MHz), a second scan segment of frequencies 129, 130, 131, . . . , 190, 191, and 192 ($\Delta f=15.625$ MHz), and a third scan segment of frequencies 196, 200, 204, . . . , 248, 252, and 256 ($\Delta f=62.5$ MHz). Reflections corresponding to the transmitted frequency pulses are received in the same sequential order at the receiver (RX) of the sensor system 1810 and processed. With reference to the receive operation, FIG. 18B illustrates that the discrete frequency pulses of the transmitted stream are received in the same sequential order (in time) as they are transmitted. The receiver, RX, then places ranging data in a "ranging data bucket" 1820 and places imaging data in a different "imaging data bucket" 1822. In particular, as illustrated in FIG. 18A, the ranging scan involves discrete frequency pulses at a step size of 62.5 MHz across the frequency range of 2-6 GHz and the imaging scan involves discrete frequency pulses at a step size of 15.625 MHz across the frequency range of 4-5 GHz. Thus, with reference to the left side of the receive operation, the portion of digital data that corresponds to the ranging data is placed in a data ranging bucket that includes data corresponding to the discrete frequencies of 4, 8, 12, . . . 248, 252, and 256 (based on RS256) and the portion of digital data that corresponds to the imaging data is placed in an imaging data bucket that includes data corresponding to the discrete frequencies of 129, 130, 131, . . . , 190, 191, and 192 (based on RS256). In this example, the discrete frequencies of 132, 136, 140, . . . , 184, 188, and 192 will be placed in both the ranging data bucket and the imaging data bucket such that only the data associated with every fourth discrete frequency from the scanned range of 129, 130, 131, . . . , 190, 191, and 192 ($\Delta f=15.625$ MHz) will be placed in the data ranging bucket. In an embodiment, the demultiplexing or extracting of the data into the proper buckets for further processing is implemented in the digital baseband system or in a CPU and the ranging and imaging buckets may be implemented as logical constructs in the digital baseband system and/or the CPU. Thus, the digital control of step size and frequency range in a stepped frequency radar system enables simultaneous capture of ranging data and imaging data via a non-overlapping stepped frequency scanning operation using a single sensor system. Although the demultiplexing or extracting of stepped frequency scanning data into specific buckets is described with reference to simultaneous capture of ranging and imaging data, the concept of demultiplexing or extracting of stepped frequency scanning data into specific buckets for subsequent processing can be implemented for other applications.

Figure 18C:
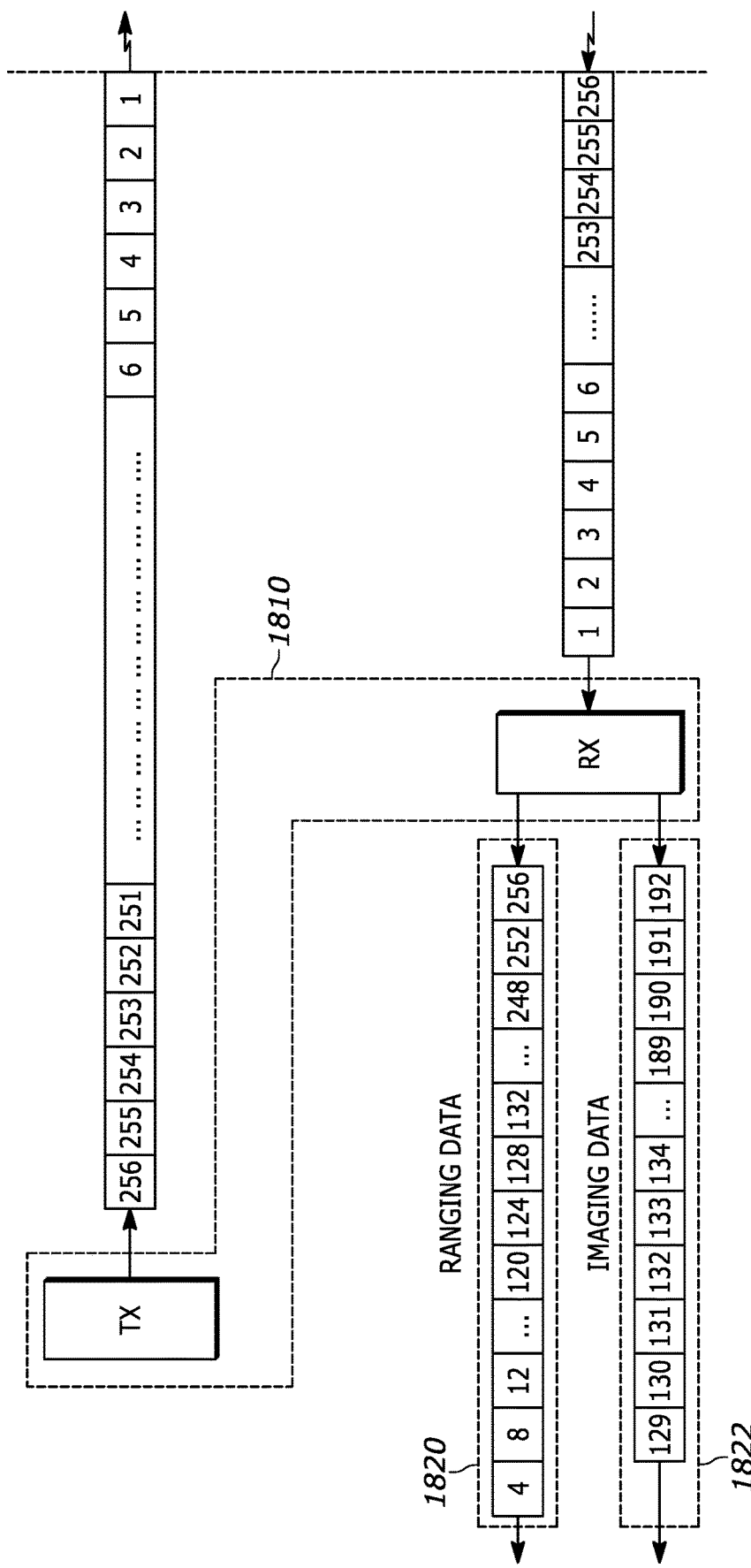
FIG. 18C illustrates another example of digital frequency coding for the stepped frequency scanning illustrated in FIG. 18A.

In an embodiment, the entire frequency range, e.g., the entire 2-6 GHz frequency range, could be scanned with a step size of, for example, $\Delta f=16.625$ MHz (RS256), and ranging and imaging data could be extracted at different multiples of the step size from the set of digital data that is generated from the scan. For example, for ranging, only data generated from every fourth frequency pulse is processed, e.g., a step size of $\Delta f=62.5$ MHz, and for imaging, data generated from every frequency pulse in the 4-5 GHz frequency range is processed, e.g., a step size of $\Delta f=16.625$ MHz in the 4-5 GHz frequency range. In an embodiment, the multiples used for extraction are integer multiples, e.g., 1, 2, 3, 4, etc. of the step size at which the frequency range was scanned. FIG. 18C illustrates digital frequency coding (in a time sequence) for the stepped frequency scanning illustrated in FIG. 18A in which a single stepped frequency scan is performed across the 2-6 GHz frequency range at a step size of $\Delta f=16.625$ MHz (RS256). At the transmitter (TX), discrete frequencies are stepped at 16.625 MHz/step across the entire 2-6 GHz frequency range. Using the RS256 scale, the discrete frequency pulses are identified as 1, 2, 3, 4, . . . 253, 254, 255, 256. Reflections corresponding to the transmitted frequency pulses are received in the same sequential order at the receiver (RX) of the sensor system 1810 and processed. With reference to the receive operation, FIG. 18C illustrates that the discrete frequency pulses of the transmitted stream are received in the same sequential order (in time) as they are transmitted. The receiver then places ranging data in a "ranging data bucket" 1820 and places imaging data in a different "imaging data bucket" 1822. In particular, as illustrated in FIG. 18A, the ranging scan involves discrete frequency pulses at a step size of 62.5 MHz across the frequency range of 2-6 GHz and the imaging scan involves discrete frequency pulses at a step size of 15.625 MHz across the frequency range of 4-5 GHz. Thus, with reference to the left side of the receive operation, the portion of digital data that corresponds to the ranging data is placed in the data ranging bucket 1820 that includes data corresponding to the discrete frequencies of 4, 8, 12, . . . 248, 252, and 256 (based on RS256) (e.g., an extraction multiple of "4" over the frequency range of interest) and the portion of digital data that corresponds to the imaging data is placed in the imaging data bucket 1822 that includes data corresponding to the discrete frequencies of 129, 130, 131, . . . , 190, 191, and 192 (based on RS256) (e.g., an extraction multiple of "1" over the frequency range of interest). In this example, the discrete frequencies of 132, 136, 140, . . . , 184, 188, and 192 will be placed in both the ranging data bucket and the imaging data bucket and only the data associated with every fourth discrete frequency will be placed in the data ranging bucket. The demultiplexing or extracting of the data into the proper buckets for further processing is implemented in digital baseband system or in a CPU and the ranging and imaging buckets may be implemented as logical constructs in the digital baseband system and/or the CPU. Thus, the digital control of step size and frequency range in a stepped frequency radar system enables simultaneous capture of ranging data and imaging data via a non-overlapping stepped frequency scanning operation using a single sensor system.

Figure 19A:
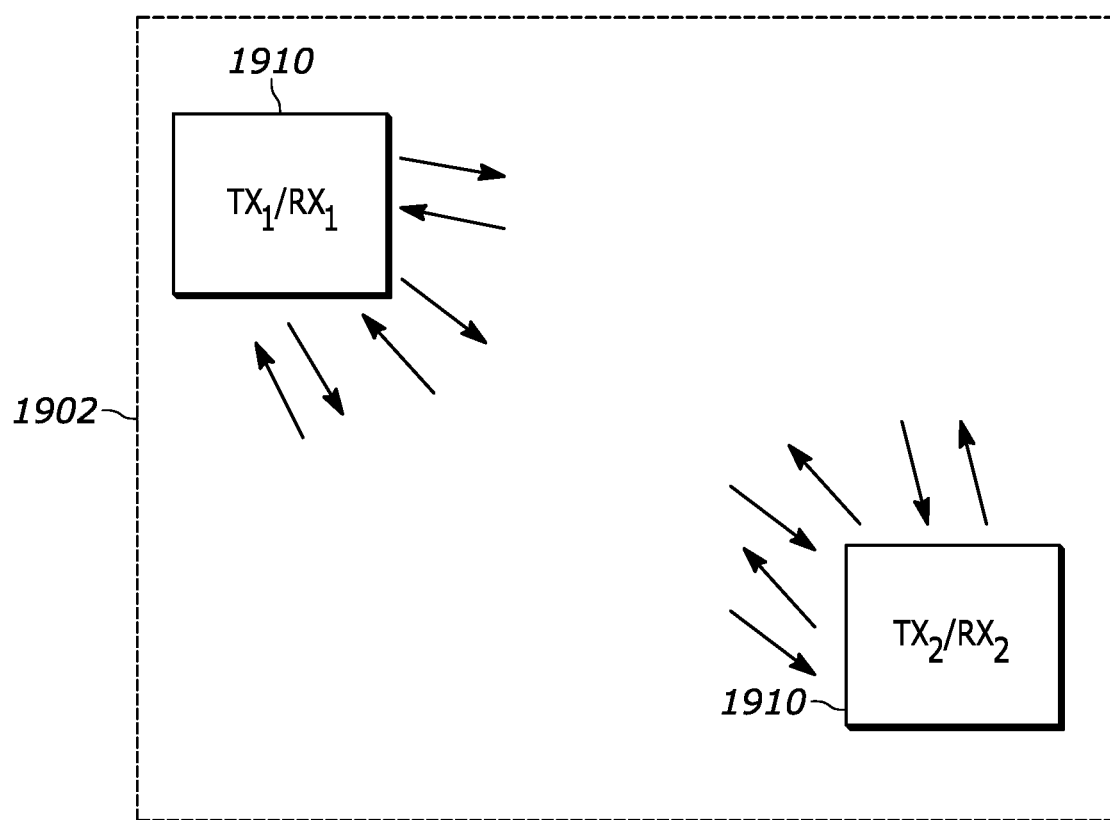
FIG. 19A depicts an area that includes two sensor systems, such as the sensor systems described with reference to FIGS. 6-8, which may interfere with each other.

In an embodiment, multiple sensor systems such as the sensor system described with reference to FIGS. 6-8 may be located near enough to each other such that the transmitted stepped frequency pulses may interfere with one another. For example, the sensor systems may be located near enough to each other in a house or building that transmitted frequency pulses and reflected RF energy may intermingle between the two sensor systems. FIG. 19A depicts an area 1902 (such as a room, a house, or a building) that includes two sensor systems (including $TX_1/RX_1$ and $TX_2/RX_2$), such as the sensor systems described above with reference to FIGS. 6-8, which may interfere with each other during stepped frequency scanning. Thus, if $TX_1$ and $TX_2$ transmit frequency pulses at the same discrete frequency and at the same time, the receivers, $RX_1$ and $RX_2$, may experience interference, which may degrade the quality of the ranging and/or imaging of the stepped frequency radar systems. However, in an embodiment, digital control of the frequencies of the discrete frequency pulses is used to encode the frequencies of the frequency pulses, e.g., in a preprogrammed or pseudorandom fashion, so that the frequency pulses of the two sensor systems are less likely or unlikely to interfere with each other. That is, the frequency pulses are not transmitted in-order or in-step, e.g., in sequential order (i.e., one step size increment per frequency pulse transmission), but rather are transmitted "out-of-order" or "out-of-step," which can reduce the likelihood of two frequency pulses from two different sensor systems interfering with each other.

Figure 19B:
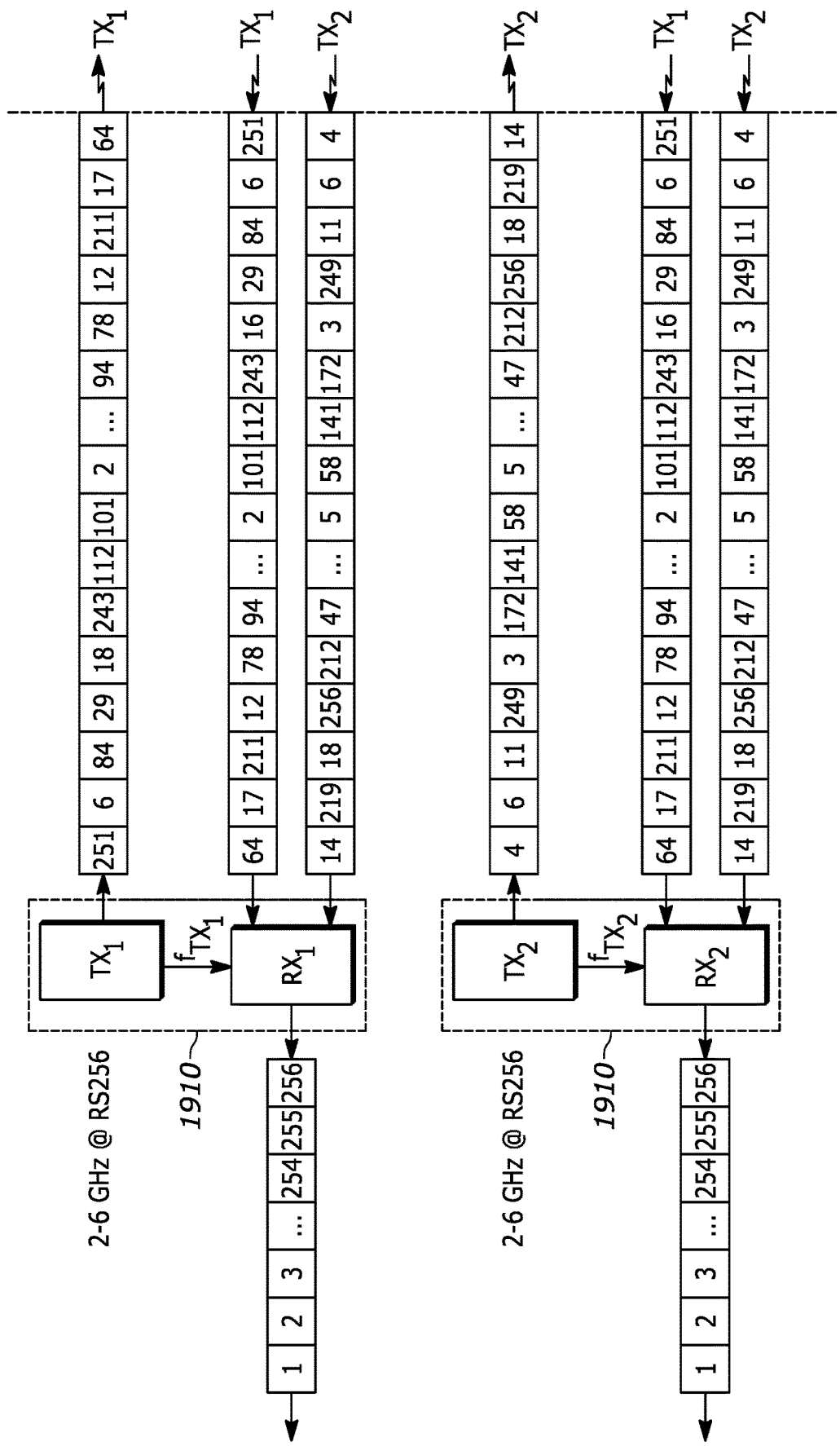
FIG. 19B illustrates encoding and corresponding decoding of discrete frequency pulses transmitted from the two sensor systems depicted in FIG. 19A.

FIG. 19B illustrates encoding and corresponding decoding of discrete frequency pulses transmitted from $TX_1$ and $TX_2$ of the sensor systems 1910 depicted in FIG. 19A. In the example of FIG. 19B, both $TX_1$ and $TX_2$ are simultaneously scanning across the 2-6 GHz frequency range at a step size of 15.625 MHz/step (e.g., RS256). Thus, each transmitter will transmit 256 discrete frequency pulses to complete a scan across the entire 2-6 GHz frequency range, with the discrete frequency pulses being identified by the numeric values of 1-256. As illustrated in FIG. 19B, $TX_1$ transmits the 256 discrete frequency pulses in a first pseudorandom order (e.g., 64, 17, 211, 12, 78, 94, . . . 2, 101, 112, 243, 16, 29, 84, 6, 251) and simultaneously with $TX_1$, $TX_2$ transmits the same 256 discrete frequency pulses in a second pseudorandom order (e.g., 14, 219, 18, 256, 212, 47, . . . 5, 58, 141, 172, 3, 249, 11, 6, 4). In a case where the two sensor systems 1910 are close enough to each other, interfering RF energy (either reflected RF energy or RF energy directly from the other transmitter) may be received at the sensor systems. For example, with reference to $RX_1$, RF energy corresponding to the stream of discrete frequencies transmitted from $TX_1$ and RF energy corresponding to the stream of discrete frequencies transmitted from $TX_2$ may be received simultaneously at $RX_1$. However, because the receivers are using stepped frequency radar, $RX_1$ is simultaneously receiving on the same frequency at which $TX_1$ is transmitting such that when $TX_1$ transmits at frequency 64, $RX_1$ receives at frequency 64. $RX_1$ may also be simultaneously exposed to RF energy at frequency 14 (generated from $TX_2$), but the RF energy at frequency 14 will not be received (e.g., will not interfere with receiving RF energy at frequency 64) since frequency 14 does not match the current transmission frequency ($f_{TX1}$=64) of $TX_1$. The receiver, $RX_1$, is then able to generate scan data associated with each transmitted frequency pulse and re-order the data in a sequential order (e.g., 1, 2, 3, . . . , 254, 255, 256) that allows ranging and/or imaging data to be gleaned from the received RF energy. As illustrated in FIG. 19B, $RX_1$ is able to re-order the data in an order that corresponds to the frequencies of the range scale, e.g., 1, 2, 3, . . . 254, 255, 256. Likewise, when $TX_2$ transmits at frequency 14, $RX_2$ receives at frequency 14. $RX_2$ may also be simultaneously exposed to RF energy at frequency 64 (generated from $TX_1$), but the RF energy at frequency 64 will not be received (e.g., will not interfere with receiving RF energy at frequency 14) since frequency 64 does not match the current transmission frequency ($f_{TX2}$=14) of $TX_2$. The receiver, $RX_2$, is then able to generate scan data associated with each transmitted frequency pulse and re-order the data in a sequential order (e.g., 1, 2, 3, . . . , 254, 255, 256) that allows ranging and/or imaging data to be gleaned from the received RF energy. As illustrated in FIG. 19B, $RX_2$ is able to re-order the data in an order that corresponds to the frequencies of the range scale, e.g., 1, 2, 3, . . . 254, 255, 256. Using the above-described technique, encoding of the discrete frequency pulses (e.g., preprogrammed or pseudorandom encoding) can be used to avoid interference between two sensor systems that are located within range of each other. In the example of FIG. 19B, given a pseudorandom pattern of 256 discrete frequencies, the likelihood of the two sensor systems transmitting frequency pulses at the same frequency at the same time can be estimated as $1/256 \times 1/256 = 1.5 \times 10^{-7}$ chance of interference. Although the example is described with only two sensor systems, the encoding scheme can be applied to more than two sensor systems and still provide a high degree of protection against interference amongst sensor systems. In an embodiment, pseudorandom encoding may implemented by pseudorandom number generators located within the sensor systems.

In an embodiment, ranging refers to detecting the linear distance between an object of interest and the sensor system using stepped frequency scanning and imaging refers to detecting the spatial spread of an object of interest relative to the sensor system. In a three dimensional coordinate system of x, y, and z, the ranging or range of an object relative to a sensor system may be represented by digital information that corresponds to a linear distance relative to the z axis and the imaging or image of an object relative to the sensor system may be represented by digital information that corresponds to the x and y dimensions of the object. In an embodiment, 2D imaging may refer to information corresponding to the x and y dimensions of an object without ranging information and 3D imaging may refer to information that combines ranging information with 2D imaging information to produce three-dimensional information about an object relative to the sensor system.

Figure 20:
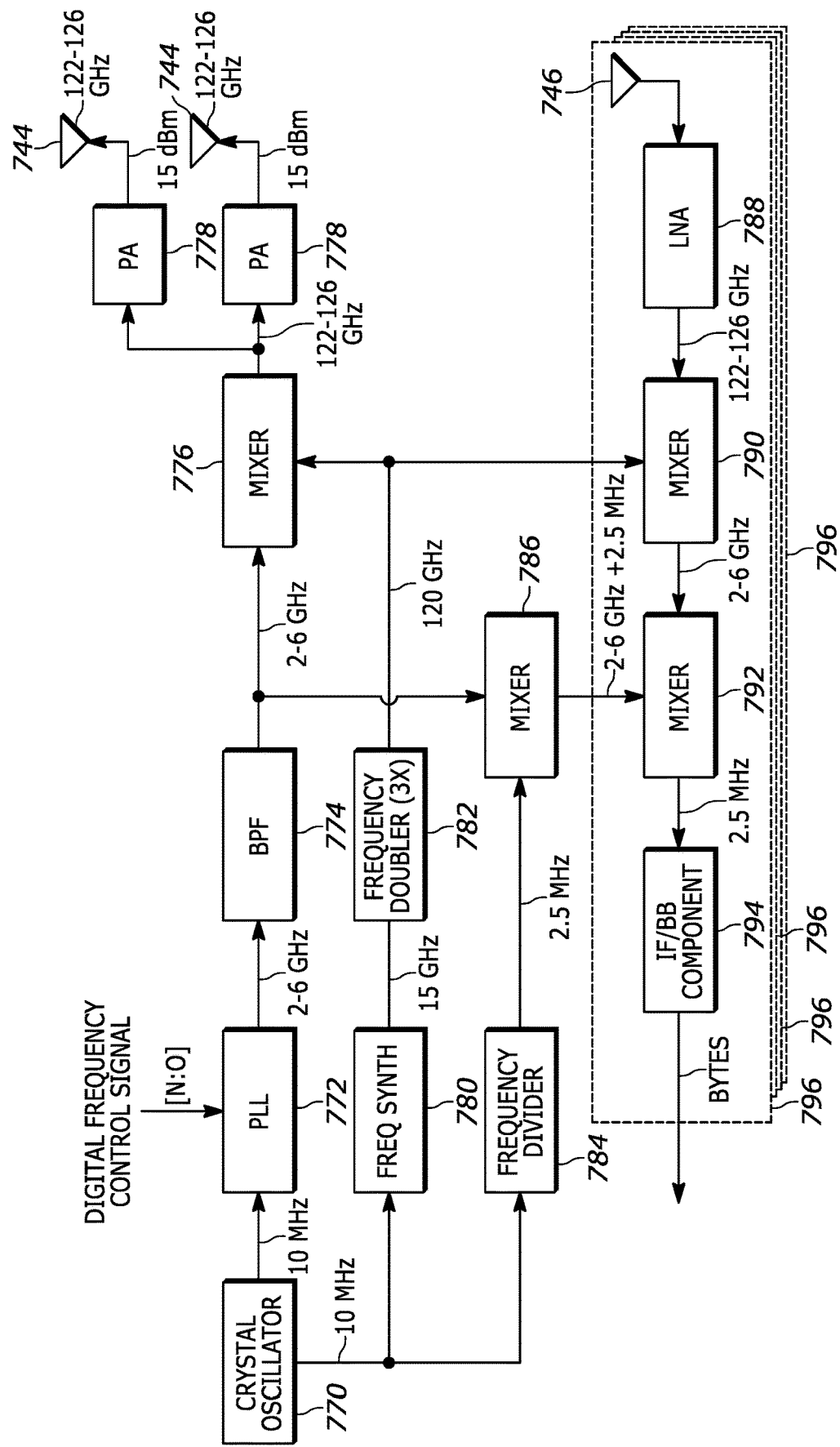
FIG. 20 depicts an expanded view of an embodiment of portions of the sensor system of FIG. 6, including elements of the RF front-end.

In an embodiment, an RF front-end is configured to support a wider range of frequencies. FIG. 20 depicts and embodiment of an RF front-end that is configured to support a 2-6 GHz frequency range and a 122-126 GHz frequency range. The RF front-end is similar to the FR front-end described with reference to FIG. 7 and thus similar reference numbers are used to identify similar components. In the embodiment of FIG. 20, the elements include a crystal oscillator 770, a phase locked loop (PLL) 772, a bandpass filter (BPF) 774, a mixer 776, power amplifiers (PAs) 778, TX antennas 744, a frequency synthesizer 780, a frequency doubler 782, a frequency divider 784, a mixer 786, an RX antenna 746, a low noise amplifier (LNA) 788, a mixer 790, a mixer 792, and an Intermediate Frequency/Baseband (IF/BB) component 794. As illustrated in FIG. 20, the group of receive components identified within and dashed box 796 is repeated four times, e.g., once for each of four distinct RX antennas.

Operation of the system shown in FIG. 20 is described with reference to a transmit operation and with reference to a receive operation. The description of a transmit operation generally corresponds to a left-to-right progression in FIG. 20 and description of a receive operation generally corresponds to a right-to-left progression in FIG. 20. With regard to the transmit operation, the crystal oscillator 770 generates an analog signal at a frequency of 10 MHz. The 10 MHz signal is provided to the PLL 772, to the frequency synthesizer 780, and to the frequency divider 784. The PLL uses the 10 MHz signal to generate an analog signal that is in the 2-6 GHz frequency range. The 2-6 GHz signal is provided to the BPF 774, which filters the input signal and passes a signal in the 2-6 GHz range to the mixer 776. The 2-6 GHz signal is also provided to the mixer 786.

Dropping down in FIG. 20, the 10 MHz signal is used by the frequency synthesizer 780 to produce a 15 GHz signal. The 15 GHz signal is used by the frequency doubler 782 to generate a signal at 120 GHz. In an embodiment, the frequency doubler includes a series of three frequency doublers that each double the frequency, e.g., from 15 GHz to 30 GHz, and then from 30 GHz to 60 GHz, and then from 60 GHz to 120 GHz. The 120 GHz signal and the 2-6 GHz signal are provided to the mixer 776, which mixes the two signals to generate a signal at 122-126 GHz depending on the frequency of the 2-6 GHz signal. The 122-126 GHz signal output from the mixer 776 is provided to the power amplifiers 778, and RF signals in the 122-126 GHz range are output from the TX antennas 744. In an embodiment, the 122-126 GHz signals are output at 15 dBm (decibels (dB) with reference to 1 milliwatt (mW)). In an embodiment, the PLL is controlled to generate discrete frequency pulses between 2-6 GHz that are used for stepped frequency transmission.

The 10 MHz signal from the crystal oscillator 770 is also provided to the frequency divider 784, which divides the frequency down, e.g., from 10 MHz to 2.5 MHz via, for example, two divide by two operations, and provides an output signal at 2.5 MHz to the mixer 786. The mixer 786 also receives the 2-6 GHz signal from the BPF 774 and provides a signal at 2-6 GHz+2.5 MHz to the mixer 792 for receive signal processing.

With reference to a receive operation, electromagnetic (EM) energy is received at the RX antenna 746 and converted to electrical signals, e.g., voltage and current. For example, electromagnetic energy in the 122-126 GHz frequency band is converted to an electrical signal that corresponds in frequency (e.g., GHz), magnitude (e.g., power in dBm), and phase to the electromagnetic energy that is received at the RX antenna. The electrical signal is provided to the LNA 788. In an embodiment, the LNA amplifies signals in the 122-126 GHz frequency range and outputs an amplified 122-126 GHz signal. The amplified 122-126 GHz signal is provided to the mixer 790, which mixes the 120 GHz signal from the frequency doubler 782 with the received 122-126 GHz signal to generate a 2-6 GHz signal that corresponds to the electromagnetic energy that was received at the RX antenna. The 2-6 GHz signal is then mixed with the 2-6 GHz+2.5 MHz signal at mixer 792 to generate a 2.5 MHz signal that corresponds to the electromagnetic energy that was received at the RX antenna. For example, when a 122 GHz signal is being transmitted from the TX antennas and received at the RX antenna, the mixer 792 receives a 2 GHz signal that corresponds to the electromagnetic energy that was received at the antenna and a 2 GHz+2.5 MHz signal from the mixer 786. The mixer 792 mixes the 2 GHz signal that corresponds to the electromagnetic energy that was received at the RX antenna with the 2 GHz+2.5 MHz signal from the mixer 786 to generate a 2.5 MHz signal that corresponds to the electromagnetic energy that was received at the RX antenna. The 2.5 MHz signal that corresponds to the electromagnetic energy that was received at the RX antenna is provided to the IF/BB component 794 for analog-to-digital conversion. The above-described receive process can be implemented in parallel on each of the four receive paths 796. As is described here, the system described with reference to FIG. 20 can be used to generate various discrete frequencies that can be used to implement, for example, stepped frequency radar detection. As described herein, multiple mixing operations are performed to implement a sensor system at such a high frequency, e.g., in the 122-126 GHz range. The multiple mixers and corresponding mixing operations implement a "compound mixing" architecture that enables use of such high frequencies.

In an embodiment, the sensor system, or components thereof, can be combined with other sensor systems to form a sensor system that includes a larger sensor array. For example, multiple sensor systems, such as the sensor systems as described above, can be arranged into a 2D array to form a multi-sensor sensor system. In one embodiment, four sensor systems are configured in a rectangular 2D array, such that the combined array includes eight TX antennas and sixteen RX antennas. FIG. 23A depicts an embodiment of a 2×2 array of sensor systems 2110 (also referred to as RF units, or RFUs) such as the sensors systems described above along with a frequency controller 2104 that combine to form a multi-sensor sensor system. In an embodiment, the frequency controller can individually control the scanning frequencies of each of the RF units. For example, the RF units can be controlled to simultaneously transmit frequency pulses at different frequencies to implement stepped frequency scanning in a manner that avoids interference amongst the RF units. The frequency controller can be implemented in hardware, software, firmware, or a combination thereof.

Figure 21A:
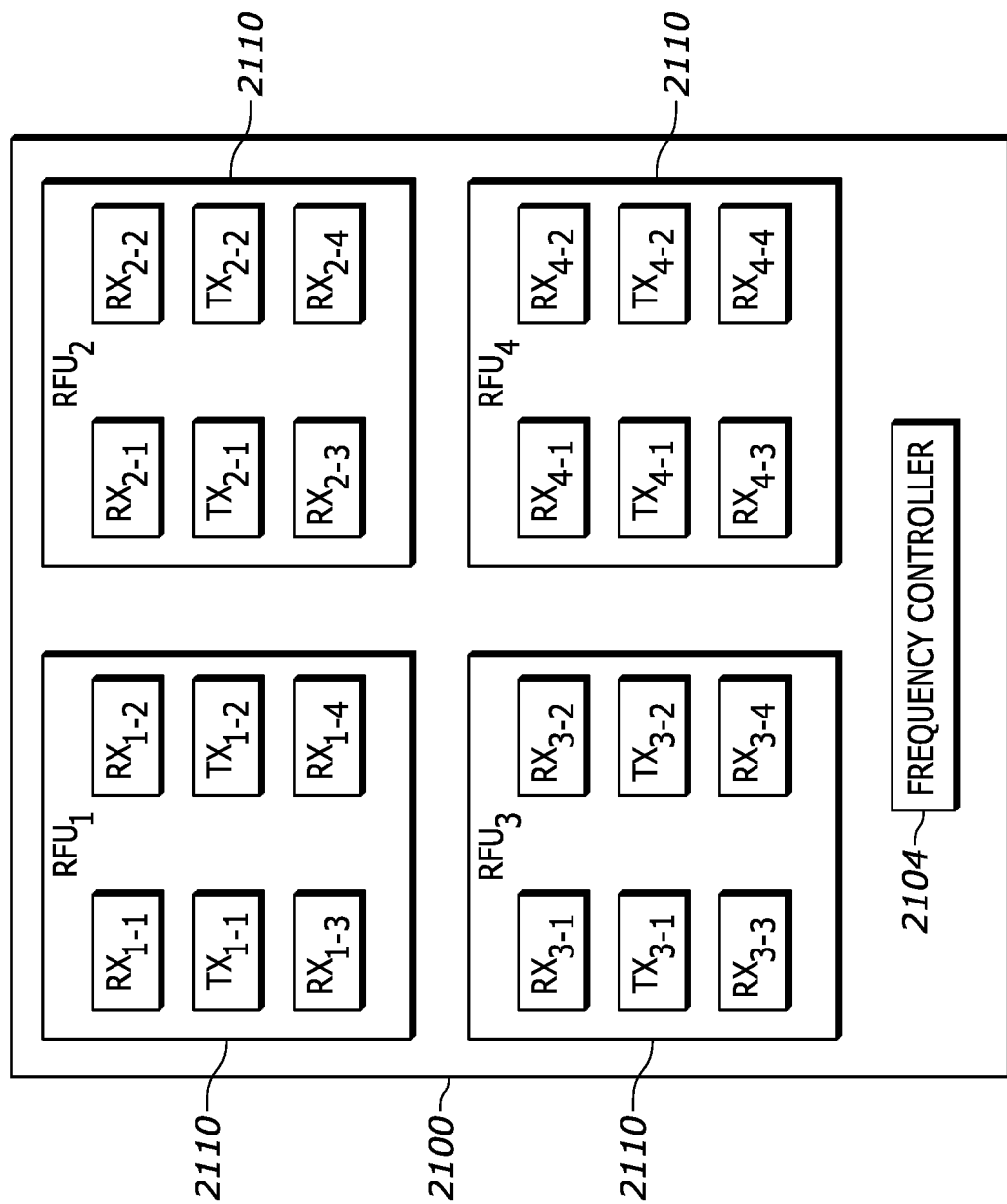
FIG. 21A depicts and embodiment of a 2×2 array of sensor systems such as the sensors systems described with reference to FIGS. 6-8.
Figure 21B:
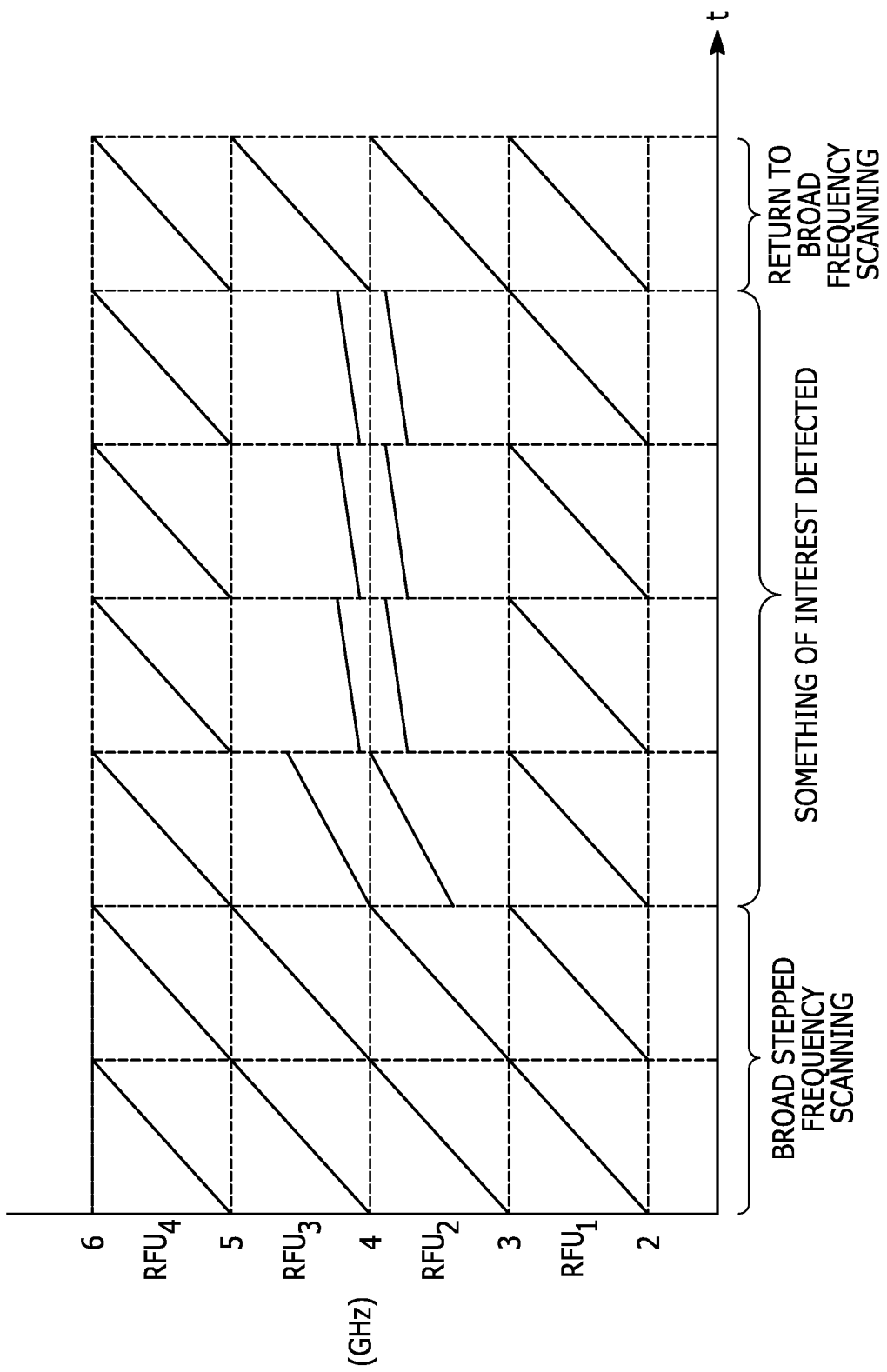
FIG. 21B illustrates an example of transmission frequency diversity that can be implemented by the sensor array of FIG. 23A.

As described above, the frequency controller 2104 can control the RF units 2110 to simultaneously transmit frequency pulses at different frequencies to implement stepped frequency scanning in a manner that avoids interference amongst the RF units. FIG. 21B illustrates an example operating scenario (in a graph of frequency vs. time) in which the RF units simultaneously implement stepped frequency scanning across different frequency sub-bands of the 2-6 GHz frequency band in a manner that avoids interference. As illustrated in FIG. 23B, RF unit 1 transmits stepped frequency pulses in the frequency range of 2-3 GHz, RF unit 2 transmits stepped frequency pulses in the frequency range of 3-4 GHz, RF unit 3 transmits stepped frequency pulses in the frequency range of 4-5 GHz, and RF unit 4 transmits stepped frequency pulses in the frequency range of 5-6. In the operating scenario illustrated in FIG. 21B, all of the RF units scan across their corresponding frequency ranges using a first step size, e.g., $\Delta f=15.625$ MHz/step (e.g., RS256) for a period of time that corresponds to two full sweeps of the corresponding frequency ranges. The same step size amongst the four RF units is represented in that the scan lines all have the same slope. Then, within the frequency ranges covered by RF units 2 and 3, there is something of interest detected from the received signals. For example, the scanning may have detected a person and/or a person carrying on object of interest such as a weapon. Thus, as illustrated in FIG. 21B, the RF units 2 and 3 change their step sizes to smaller step sizes and to narrow frequency ranges at targeted frequency bands, which smaller step sizes and targeted frequency bands may be better for identifying objects such as weapons. As illustrated in FIG. 21B, the smaller step sizes for RF units 2 and 3 are represented by the lower slope of the scan lines that correspond to the stepped frequency scanning during the period of time that corresponds to the next four sweeps and the smaller frequency ranges and targeted frequency bands are represented by the vertical displacement (frequency range) and vertical location (targeted frequency bands) of the scan lines. Additionally, the step sizes implemented by the RF units may change as indicated by the change in slope between the third sweep and the fourth sweep. At some point, the sensor system may decide to return to a sweep configuration that is better suited for ranging as opposed to imaging. FIG. 21B illustrates that in sweep seven, all of the RF units in the system return to sweeping across their original frequency bands at the original step size, e.g., $\Delta f=15.625$ MHz/step (e.g., RS256), which may be better suited for ranging as opposed to imaging. As illustrated in FIG. 21B, the four RF units perform simultaneous stepped frequency scanning across non-interfering frequency ranges in a manner that enables multiple frequency bands to be simultaneously scanned without interfering with each other. Thus, digital control of discrete frequencies in a stepped frequency radar system provides spectral agility that can be utilized to implement a multi-sensor system that can be used to implement ranging and 2D or 3D scanning in useful applications such as security monitoring.

Figure 22:
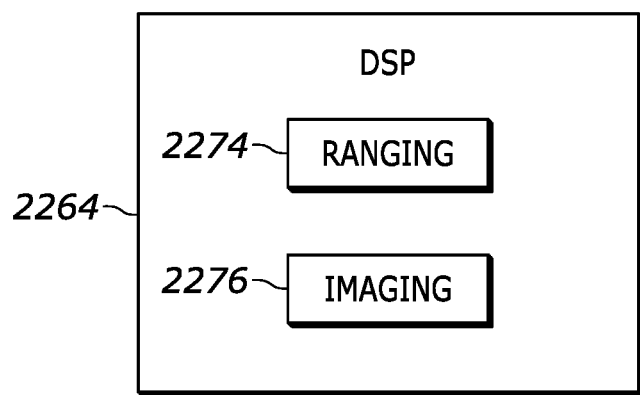
FIG. 22 is an embodiment of a DSP that includes a ranging component and an imaging component.

In an embodiment, signal processing to implement ranging and 2D or 3D imaging can be implemented in part or in full digitally by a DSP and/or a CPU. FIG. 22 is an embodiment of a DSP 2264 that includes a ranging component 2274 and an imaging component 2276. Although the DSP is shown as including the two components, the DSP may include fewer components and the DSP may include other digital signal processing capability. The DSP may include hardware, software, and/or firmware or a combination thereof that is configured to implement the digital signal processing that is described herein. In an embodiment, the DSP may be embodied as an ARM processor (Advanced RISC (reduced instruction set computing) Machine). In some embodiments, components of a DSP can be implemented in the same IC device as the RF front-end and the TX and RX antennas. In other embodiments, components of the DSP are implemented in a separate IC device or IC devices.

In an embodiment, the transmission of millimeter radio waves and the processing of signals that correspond to received radio waves is a dynamic process that operates to locate signals corresponding to the desired object (e.g., a person and/or a person carrying a weapon) and to improve the quality of the desired signals (e.g., to improve the SNR). For example, the process is dynamic in the sense that the process is an iterative and ongoing process as the location of the sensor system relative to a vein or veins changes.

Beamforming is a signal processing technique used in sensor arrays for directional signal transmission and/or reception. Beamforming can be implemented by combining elements in a phased antenna array in such a way that signals at particular angles experience constructive interference while other signals experience destructive interference. Beamforming can be used in both transmit operations and receive operations in order to achieve spatial selectivity, e.g., to isolate some received signals from other received signals.

In an embodiment, the techniques described herein are application to monitoring a health parameter of a person, for example, monitoring the blood glucose level in a person, or to monitoring other parameters of a person's health such as, for example, blood pressure and heart rate. For example, the reflectively of blood in a vessel such as the basilic vein will change relative to a change in blood pressure. The change in reflectivity as monitored by the sensor system can be correlated to a change in blood pressure and ultimately to an absolute value of a person's blood pressure. Additionally, monitored changes in blood pressure can be correlated to heart beats and converted over time to a heart rate, e.g., in beats per minute. In other embodiments, the disclosed techniques can be used to monitor other parameters of a person's health that are affected by the chemistry of the blood. For example, the disclosed techniques may be able to detect changes in blood chemistry that correspond to the presence of foreign chemicals such as alcohol, narcotics, *Cannabis*, etc. The above-described techniques may also be able to monitor other parameters related to a person, such as biometric parameters.

The above-described techniques may be used to monitor a health parameter (or parameters) related to blood in a blood vessel or in blood vessels of a person. The blood vessels may include, for example, arteries, veins, and/or capillaries. The health monitoring technique can target blood vessels such as the basilic and/or cephalic veins and/or vessels other than the basilic and/or cephalic veins. For example, other near-surface blood vessels (e.g., blood vessels in the subcutaneous layer) such as arteries may be targeted. Additionally, locations around the wrist or locations other than the wrist area can be targeted for health monitoring. For example, locations in around the ear may be a desirable location for health monitoring, including, for example, the superficial temporal vein and/or artery and/or the anterior auricular vein or artery. In an embodiment, the sensor system may be integrated into a device such as a wearable device (e.g., a watch) or another device such as a smartphone or a standalone health monitoring device.

In an embodiment, health monitoring using the techniques described above, may involve a calibration process. For example, a calibration process may be used for a particular person and a particular monitoring device to enable desired monitoring quality.

Although the techniques are described as using frequency ranges of 2-6 GHz and 122-126 GHz, some or all of the above-described techniques may be applicable to frequency ranges other than 2-6 GHz and 122-126 GHz. For example, the techniques may be applicable to frequency ranges around 60 GHz. In an embodiment, a system similar to that described with reference to FIG. 6 may be used to implement health monitoring by transmitting and receiving RF energy in the 2-6 GHz range and/or in the 122-126 GHz. For example, health monitoring may be implemented using both the 2-6 GHz frequency range and the 122-126 GHz frequency range. For example, in an embodiment, stepped frequency scanning in implemented in the lower frequency range and then in the higher frequency range, or vice versa. Using multiple non-contiguous frequency ranges (e.g., both the 2-6 GHz frequency range and the 122-126 GHz frequency range) may provide improved accuracy of health monitoring.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Alternatively, embodiments of the invention may be implemented entirely in hardware or in an implementation containing both hardware and software elements. In embodiments which use software, the software may include but is not limited to firmware, resident software, microcode, etc.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for operating a stepped frequency radar system, the method comprising:
performing a stepped frequency scan across a frequency range using at least one transmit antenna and a two-dimensional array of receive antennas and using frequency steps of a fixed step size;
processing a first portion of digital data that is generated from the stepped frequency scan across the frequency range to produce a first digital output, wherein the first portion of the digital data is derived from a series of frequency pulses of the stepped frequency scan that are separated by a first step size that is a multiple of the fixed step size; and
processing a second portion of digital data that is generated from the stepped frequency scan across the frequency range to produce a second digital output, wherein the second portion of the digital data is derived from a series of frequency pulses of the stepped frequency scan that are separated by a second step size that is a multiple of the fixed step size;
wherein the first multiple is different from the second multiple.

2. The method of claim 1, wherein the first portion of digital data is processed to generate ranging information as the first digital output and the second portion of digital data is processed to generate imaging information as the second digital output.

3. The method of claim 2, wherein the first multiple is larger than the second multiple such that the first step size is larger than the second step size.

4. A method for operating a stepped frequency radar system, the method comprising:
performing a stepped frequency scan across a frequency range using at least one transmit antenna and a two-dimensional array of receive antennas and using frequency steps of a fixed step size;
generating digital data that corresponds to the stepped frequency scan across the frequency range;
processing a first portion of the digital data that is generated from the stepped frequency scan across the frequency range to generate ranging information as a first digital output, wherein the first portion of the digital data is derived from a series of frequency pulses of the stepped frequency scanning that are separated by a first step size that is a multiple of the fixed step size;
processing a second portion of the digital data that is generated from the stepped frequency scan across the frequency range to generate imaging information as a second digital output, wherein the second portion of the digital data is derived from a series of frequency pulses of the stepped frequency scanning that are separated by a second step size that is a multiple of the fixed step size;
wherein the first multiple is larger than the second multiple such that the first step size is larger than the second step size.

* * * * *